(12) United States Patent
Li et al.

(10) Patent No.: US 10,478,458 B2
(45) Date of Patent: Nov. 19, 2019

(54) IN VITRO PRE-CONDITIONED BONE MARROW-DERIVED MESENCHYMAL STEM CELLS AND USES THEREOF

(71) Applicant: THE JOHNS HOPKINS UNIVERSITY, Baltimore, MD (US)

(72) Inventors: Xuhang Li, Clarksville, MD (US); Xiaohua Hou, Wuhan (CN); Rong Lin, Wuhan (CN)

(73) Assignees: THE JOHNS HOPKINS UNIVERSITY, Baltimore, MD (US); UNION HOSPITAL, TONGJI MEDICAL COLLEGE, HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 169 days.

(21) Appl. No.: 15/227,831

(22) Filed: Aug. 3, 2016

(65) Prior Publication Data
US 2017/0095511 A1    Apr. 6, 2017

Related U.S. Application Data

(60) Provisional application No. 62/200,464, filed on Aug. 3, 2015.

(51) Int. Cl.
| | |
|---|---|
| *A61K 35/28* | (2015.01) |
| *C12N 5/00* | (2006.01) |
| *C12N 5/0775* | (2010.01) |
| *A61K 9/00* | (2006.01) |
| *C12N 5/0793* | (2010.01) |
| *A61K 35/12* | (2015.01) |

(52) U.S. Cl.
CPC ............ *A61K 35/28* (2013.01); *A61K 9/0053* (2013.01); *C12N 5/0619* (2013.01); *C12N 5/0663* (2013.01); *A61K 2035/124* (2013.01); *C12N 2501/13* (2013.01); *C12N 2506/1353* (2013.01)

(58) Field of Classification Search
CPC .... C12N 5/0663; C12N 5/0619; A61K 35/28; A61K 9/0053
See application file for complete search history.

(56) References Cited

U.S. PATENT DOCUMENTS

| | | | | |
|---|---|---|---|---|
| 2004/0151701 | A1* | 8/2004 | Kim ..................... | C12N 5/0619 424/93.7 |
| 2010/0003751 | A1* | 1/2010 | Revel ................... | C12N 5/0619 435/368 |
| 2014/0271905 | A1* | 9/2014 | Bitar .................... | C12N 5/0619 424/520 |

OTHER PUBLICATIONS

Gao et al., Chin J Dig Dis 2006, 7 (3): 156-163, "Differentiation potential of bone marrow stromal cells to enteric neurons in vitro" (Year: 2006).*
Scintu et al., BMC Neuroscience 2006 7:14, 1-12, "Differentiation of human bone marrow stem cells into cells with a neural phenotype: diverse effects of two specific treatments" (Year: 2006).*
Laranjeira et al. Enteric nervous system development: Recent progress and future challenges. Auton Neurosci 151 : 61-69. 2009.
Heanue et al. Enteric nervous system development and Hirschsprung's disease: advances in genetic and stem cell studies. Nat Rev Neurosci 8: 466-479. 2007.
Camilleri et al. Enteric neurodegeneration in ageing. Neurogastroenterol Motil 20: 418-429. 2008.
Lebouvier et al. The second brain and Parkinson's disease. Eur J Neurosci 30: 735-741. 2009.
Pasricha. Desperately seeking serotonin . . . A commentary on the withdrawal of tegaserod and the state of drug development for functional and motility disorders. Gastroenterology 132: 2287-2290. 2007.
Becker et al. Further promise of stem cells therapies in the enteric nervous system. Gastroenterology 136: 2055-2058. 2009.
Kulkarni et al. Stem cell transplantation in neurodegenerative disorders of the gastrointestinal tract: future or fiction? Gut 61:613-621. 2012.
Garbossa et al. Recent therapeutic strategies for spinal cord injury treatment: possible role of stem cells. Neurosurg Rev 35: 293-311; Comments 311. 2012.
Koch et al. A rosette-type, self-renewing human ES cell-derived neural stem cell with potential for in vitro instruction and synaptic integration. Proc Natl Acad Sci US A 106: 3225-3230. 2009.
Kawaguchi et al. Isolation and propagation of enteric neural crest progenitor cells from mouse embryonic stem cells and embryos. Development 137: 693-704. 2010.
Hu et al. Neural differentiation of human induced pluripotent stem cells follows developmental principles but with variable potency. Proc Natl Acad Sci USA 107: 4335-4340. 2010.
Micci et al. Neural stem cell transplantation in the stomach rescues gastric function in neuronal nitric oxide synthase-deficient mice. Gastroenterology 129: 1817-1824. 2005.
Dupin et al. Neural crest progenitors and stem cells: from early development to adulthood. Dev Biol 366: 83-95. 2012.

(Continued)

*Primary Examiner* — Ruth A Davis
(74) *Attorney, Agent, or Firm* — MH2 Technology Law Group, LLP

(57) ABSTRACT

Disclosed is a composition including: an isolated in vitro pre-conditioned population of adult bone marrow derived mesenchymal stem cells (BMSCs), wherein the BMSCs express neuronal markers, and wherein the neuronal markers are PGP9.5, NSE, Tuj1, HuC/D and neuronal nitric oxide synthase (nNOS). Methods of preparing the BMSCs are also provided. In addition, the present disclosure is directed to a method of treating an enteric nervous system-related disorder including: administering to a subject in need thereof a pharmaceutical composition including the in vitro pre-conditioned BMSC population and a pharmaceutically acceptable carrier.

20 Claims, 18 Drawing Sheets
(13 of 18 Drawing Sheet(s) Filed in Color)
Specification includes a Sequence Listing.

(56) References Cited

OTHER PUBLICATIONS

Metzger et al. Enteric nervous system stem cells derived from human gut mucosa for the treatment of aganglionic gut disorders. Gastroenterology 136: 2214-2225 e2211-2213. 2009.

Lindley et al. Human and mouse enteric nervous system neurosphere transplants regulate the function of aganglionic embryonic distal colon. Gastroenterology 135: 205-216 e206. 2008.

Ben-David et al. The tumorigenicity of human embryonic and induced pluripotent stem cells. Nat Rev Cancer 11: 268-277. 2011.

Micci et al. Neural stem cells for the treatment of disorders of the enteric nervous system: strategies and challenges. Dev Dyn 236: 33-43. 2007.

Lindvall et al. Stem cells in human neurodegenerative disorders—time for clinical translation? J Clin Invest 120: 29-40. 2010.

Scuteri et al. Mesenchymal stem cells neuronal differentiation ability: a real perspective for nervous system repair? Curr Stem Cell Res Ther 6: 82-92. 2011 (Abstract Only).

Trzaska et al. Brain-derived neurotrophic factor facilitates maturation of mesenchymal stem cell-derived dopamine progenitors to functional neurons. J Neurochem 110: 1058-1069. 2009.

Greco et al. An interdisciplinary approach and characterization of neuronal cells transdifferentiated from human mesenchymal stem cells. Stem Cells Dev 16: 811-826. 2007.

Lu et al. Induction of bone marrow stromal cells to neurons: differentiation, transdifferentiation, or artifact? J Neurosci Res 77: 174-191. 2004.

Singer et al. Mesenchymal stem cells: mechanisms of inflammation. Annu. Rev. Pathol. Mech. Dis. 6: 457-478. 2011.

Zhang et al. The challenges and promises of allogeneic mesenchymal stem cells for use as a cell-based therapy. Stem Cell Research & Therapy 6:234, pp. 1-7. 2015.

Ankrum et al. Mesenchymal stem cells: immune evasive, not immune privileged. Nat. Biotechnol. 32:252-60. doi: 10.1038/nbt.2816. 2014.

Vercelli et al. Human mesenchymal stem cell transplantation extends survival, improves motor performance and decreases neuroinflammation in mouse model of amyotrophic lateral sclerosis. Neurobiol Dis 31: 395-405. 2008.

Ninomiya et al. Intranasal delivery of bone marrow stromal cells to spinal cord lesions. J Neurosurg Spine. 23:111-119. 2015.

Shichinohe et al. Bone marrow stromal cells rescue ischemic brain by trophic effects and phenotypic change toward neural cells. Neurorehabil Neural Repair 29: 80-89. 2015.

Tanna et al. Mesenchymal stem cells: potential in treatment of neurodegenerative diseases. Curr Stem Cell Res Ther 9: 513-521, 2014 (Abstract Only).

Dasari et al. Mesenchymal stem cells in the treatment of spinal cord injuries: A review. World J Stem Cells 6: 120-133. 2014.

Maltman et al. Role of mesenchymal stem cells in neurogenesis and nervous system repair. Neurochem Int 59: 347-356. 2011.

Wurmser et al. Stem cells: cell fusion causes confusion. Nature 416: 485-487. 2002.

Sanges et al. "Cell-fusion-mediated reprogramming: pluripotency or transdifferentiation? Implications for regenerative medicine." Cell Fusion in Health and Disease. Springer Netherlands, 2011. 137-159.

Metzger. Neurogenesis in the enteric nervous system. Arch Ital Biol 148: 73-83. 2010.

Houghton et al. Gastric cancer originating from bone marrow-derived cells. Science 306: 1568-1571. 2004.

Wood. Enteric nervous system neuropathy: repair and restoration. Curr Opin Gastroenterol 27: 106-111. 2011.

Herrmann et al. Preconditioning mesenchymal stem cells with transforming growth factor-alpha improves mesenchymal stem cell-mediated cardioprotection. Shock 33: 24-30. 2010.

Liu et al. Dedifferentiation—reprogrammed mesenchymal stem cells with improved therapeutic potential. Stem Cells 29: 2077-2089. 2011.

Boopathy et al. Oxidative stress-induced Notch1 signaling promotes cardiogenic gene expression in mesenchymal stem cells. Stem Cell Res Ther 4: 43. 2013, pp. 1-14.

Bondurand et al. Neuron and glia generating progenitors of the mammalian enteric nervous system isolated from foetal and post-natal gut cultures. Development 130: 6387-6400. 2003.

Liu et al. Neuroepithelial stem cells differentiate into neuronal phenotypes and improve intestinal motility recovery after transplantation in the aganglionic colon of the rat. Neurogastroenterol Motil 19: 1001-1009. 2007.

Higham et al. Relation between cholecystokinin and antral innervation in the control of gastric emptying in the rat. Gut 41:24-32. 1997.

Long et al. Effectiveness of trimebutine maleate on modulating intestinal hypercontractility in a mouse model of postinfectious irritable bowel syndrome. Eur J Pharmacol 636: 159-165. 2010.

Depoortere et al. Comparison of the gastroprokinetic effects of ghrelin, GHRP-6 and motilin in rats in vivo and in vitro. Eur J Pharmacal 515: 160-168. 2005.

Lin et al. D-glucose acts via sodium/glucose cotransporter 1 to increase NHE3 in mouse jejunal brush border by a Na+/H+ exchange regulatory factor 2-dependent process. Gastroenterology 140: 560-571. 2011.

Alex et al. Clcn5 knockout mice exhibit novel immunomodulatory effects and are more susceptible to dextran sulfate sodiuminduced colitis. J Immunol 184: 3988-3996. 2010.

Lin et al. Bone marrow-derived mesenchymal stem cells favor the immunosuppressive T cells skewing in a Helicobacter pylori model of gastric cancer. Stem Cells Dev 22: 2836-2848. 2013.

Gaumnitz et al. Electrophysiological and pharmacological responses of chronically denervated lower esophageal sphincter of the opossum. Gastroenterology 109: 789-799. 1995.

Hanani et al. Regeneration of myenteric plexus in the mouse colon after experimental denervation with benzalkonium chloride. J Comp Neurol 462: 315-327. 2003.

Kawahara et al. Comparison of effects of a selective 5-HT reuptake inhibitor versus a 5-HT4 receptor agonist on in vivo neurogenesis at the rectal anastomosis in rats. Am J Physiol Gastrointest Liver Physiol 302: G588-G597. 2012.

Joseph et al. Enteric glia are multi potent in culture but primarily form glia in the adult rodent gut. J Clin Invest 121: 3398-3411. 2011.

Matsuyoshi et al. A 5-HT(4)-receptor activation-induced neural plasticity enhances in vivo reconstructs of enteric nerve circuit insult. Neurogastroenterol Motil 22: 806-813, e226. 2010.

Liu et al. 5-HT4 receptor-mediated neuroprotection and neurogenesis in the enteric nervous system of adult mice. J Neurosci 29: 9683-9699. 2009.

Micci et al. Caspase inhibition increases survival of neural stem cells in the gastrointestinal tract. Neurogastroenterol Motil 17: 557-564. 2005.

Rismanchi et al. (2003) Cell death and long-term maintenance of neuron-like state after differentiation of rat bone marrow stromal cells: a comparison of protocols. Brain Res 991: 46-55.

Mathur et al. A transient niche regulates the specification of *Drosophila* intestinal stem cells. Science 327: 210-213. 2010.

Shepherd et al. Roles for GFRalpha1 receptors in zebrafish enteric nervous system development. Development 131: 241-249. 2004.

Shi et al. Glial cell line-derived neurotrophic growth factor increases motility and survival of cultured mesenchymal stem cells and ameliorates acute kidney injury. Am J Physiol Renal Physiol 294: F229-235. 2008.

Satake et al. Up-regulation of glial cell line-derived neurotrophic factor (GDNF) following traumatic spinal cord injury. Neuroreport 11: 3877-3881. 2000.

Kao et al. Exogenous administration of glial cell line-derived neurotrophic factor improves recovery after spinal cord injury. Resuscitation 77: 395-400. 2008.

Roberto De Giorgio et al., "Inflammatory Neuropathies of the Enteric Nervous System", Gastroenterology, 2004: 126, pp. 1872-1883.

"Hirschsprung's disease", MayoClinic, 2019, Retrieved from the Internet: https://www.mayoclinic.org/disease-conditions/hirschsprungs-disease/symptoms-causes/syc-20351556, pp. 1-8.

(56) References Cited

OTHER PUBLICATIONS

"Hirschsprung Disease", National Institute of Diabetes and Digestive and Kidney Diseases, 2019, Retrieved from the Internet: https://www.niddk.nih.gov/health-information/digestive-diseases/hirschsprung-disease, pp. 1-12.

* cited by examiner

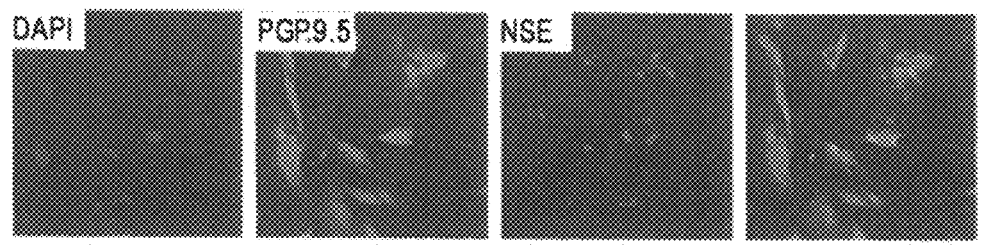
FIG. 1A
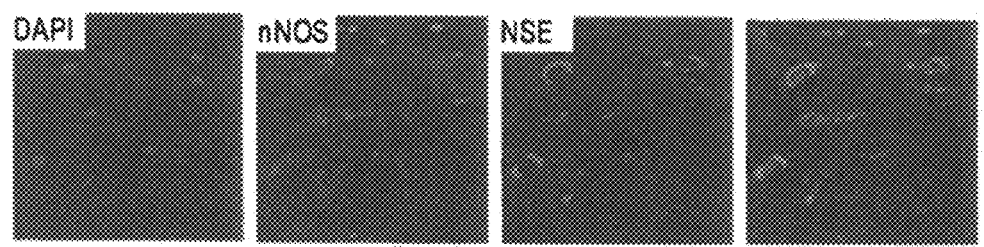
FIG. 1B
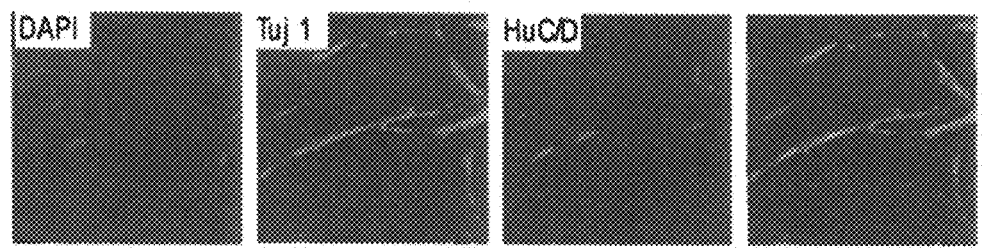
FIG. 1C
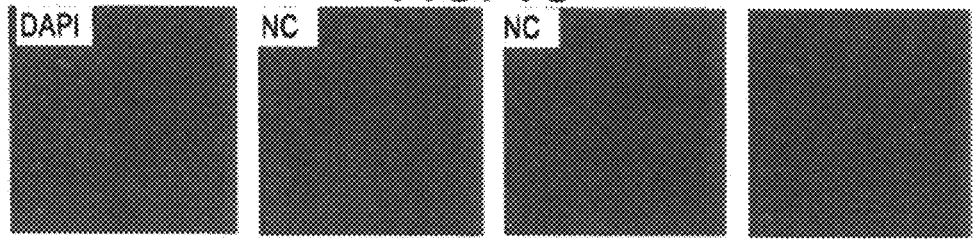
FIG. 1D
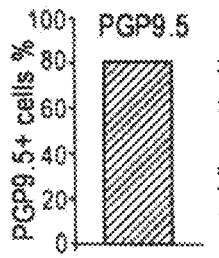 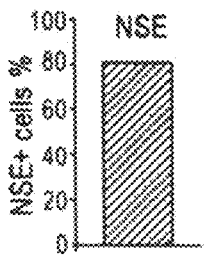 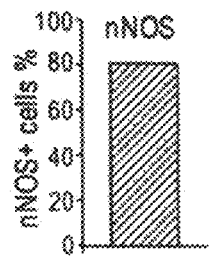 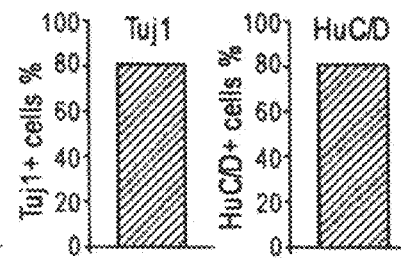 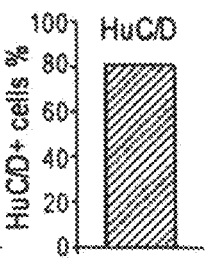
FIG. 1E  FIG. 1F  FIG. 1G  FIG. 1H  FIG. 1I

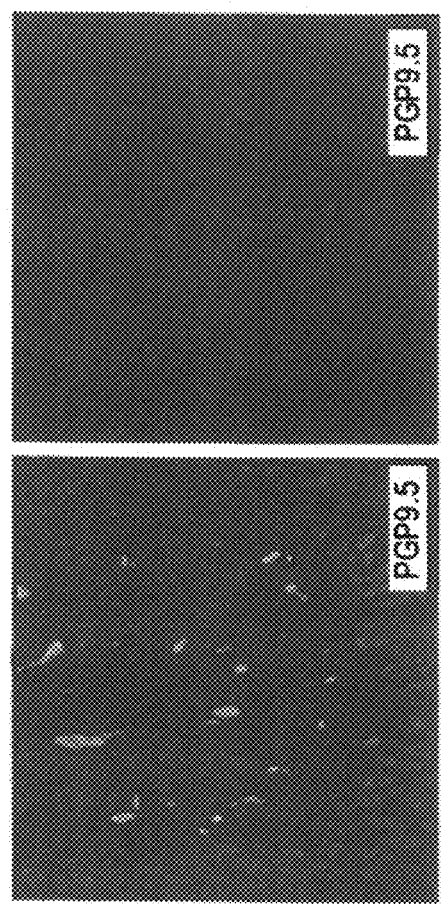
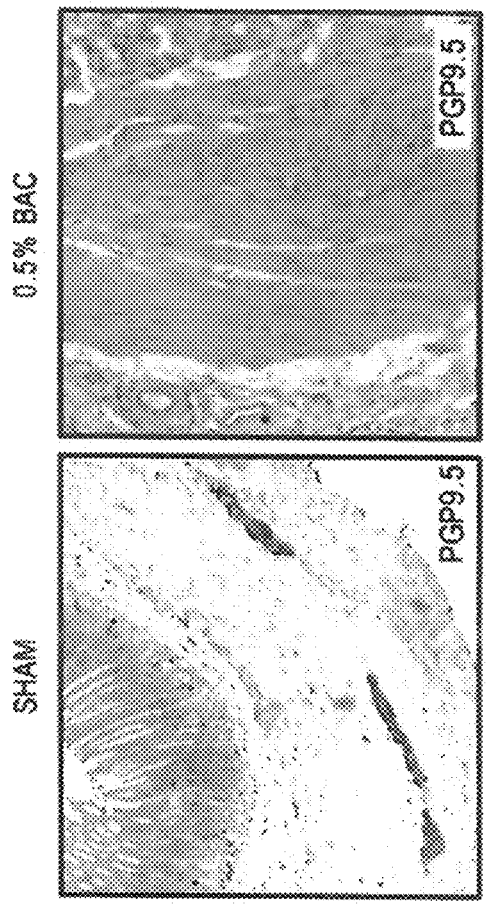
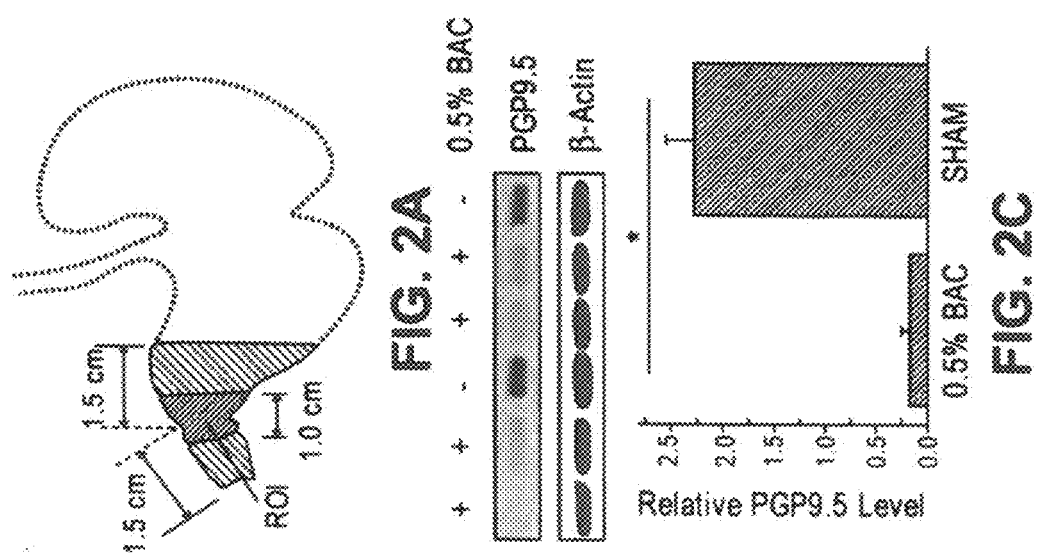
FIG. 2A
FIG. 2B
FIG. 2C

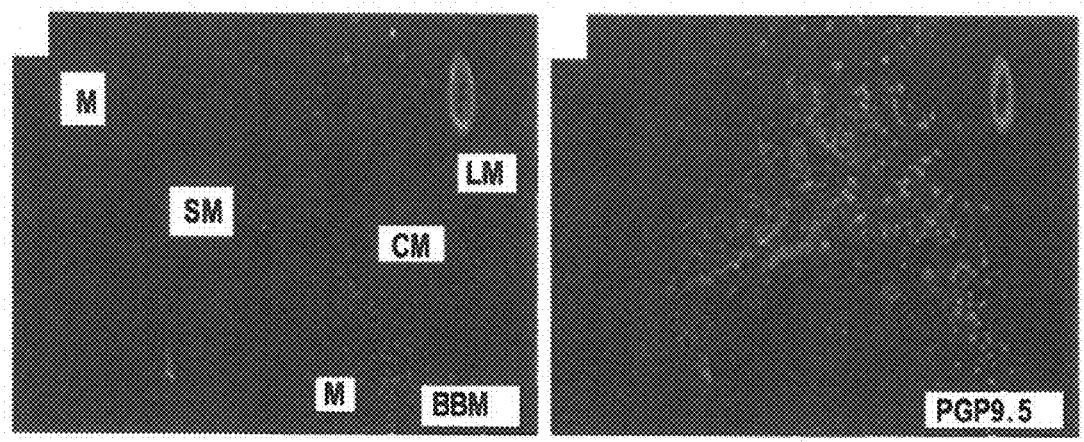
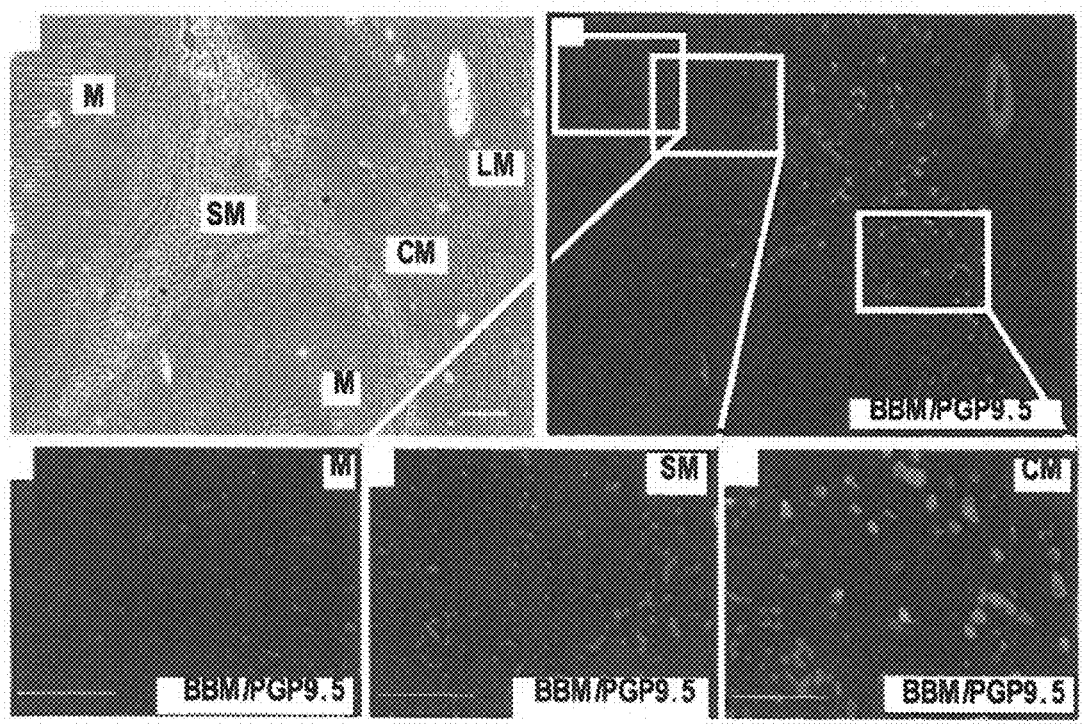

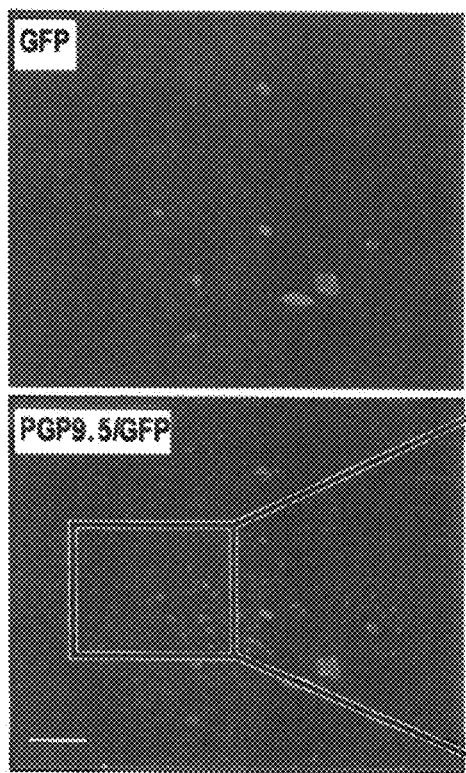
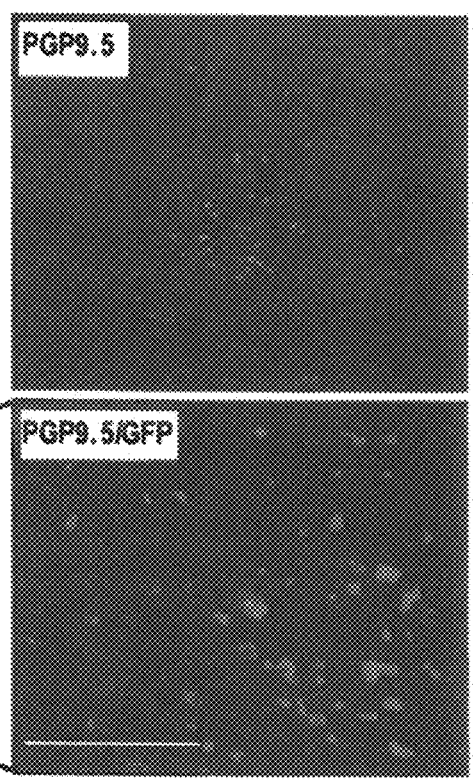
FIG. 5A  FIG. 5B
FIG. 5C  FIG. 5D

FIG. 10A Sham
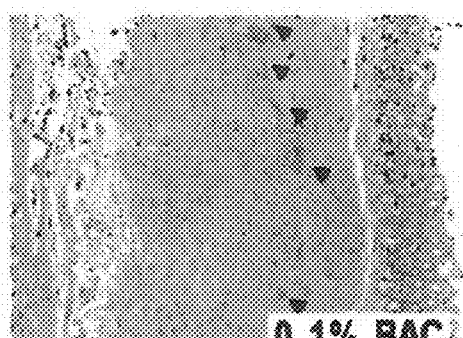
FIG. 10B 0.1% BAC
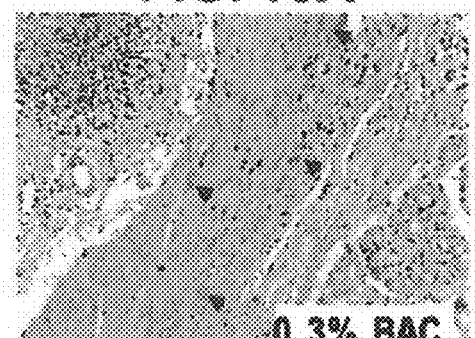
FIG. 10C 0.3% BAC
FIG. 10D 0.5% BAC
FIG. 10E Sham
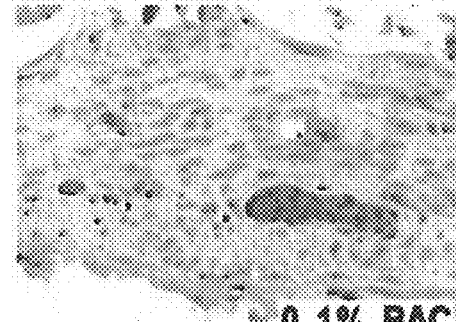
FIG. 10F 0.1% BAC
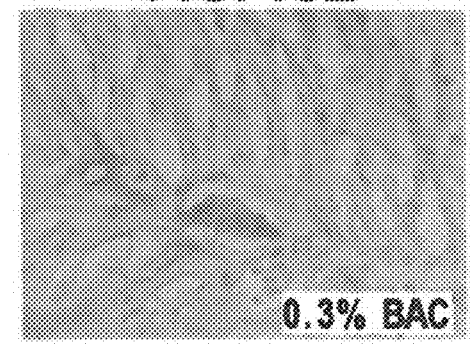
FIG. 10G 0.3% BAC
FIG. 10H 0.5% BAC

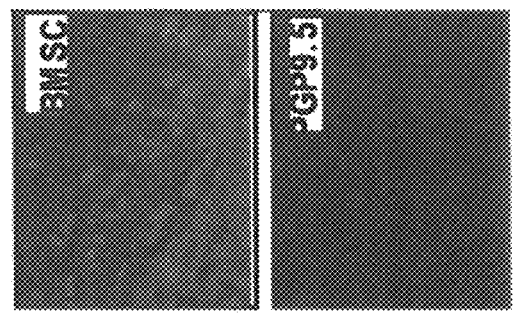
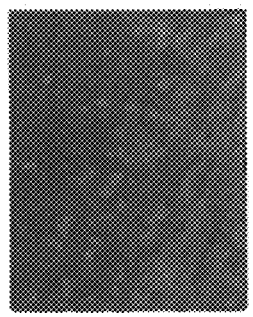
FIG. 11E  FIG. 11F  FIG. 11G
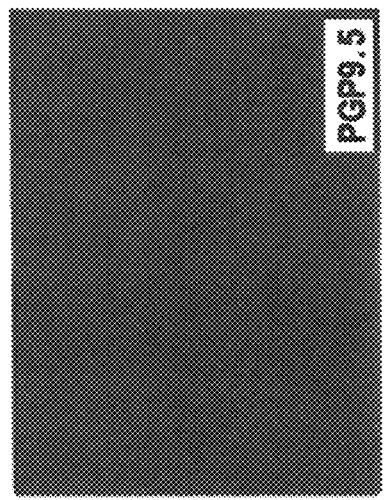
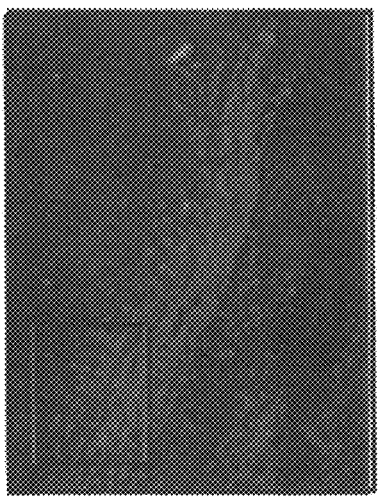
FIG. 11B  FIG. 11D
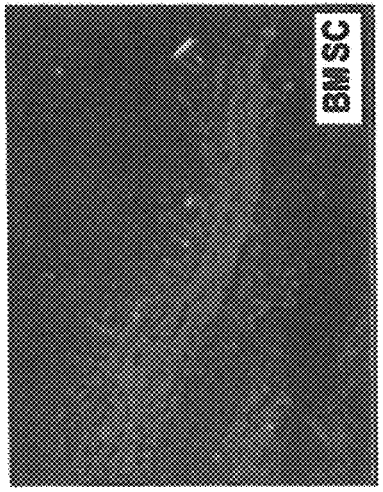
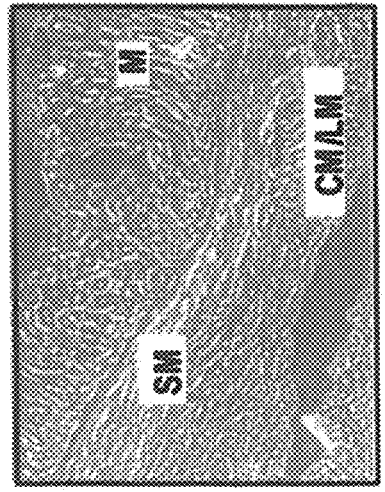
FIG. 11A  FIG. 11C Notes: M, Mucosa; SM, submucosa; CM, circular muscle; LM, longitudinal muscle; S, serosal

IN VITRO PRE-CONDITIONED BONE MARROW-DERIVED MESENCHYMAL STEM CELLS AND USES THEREOF

CROSS REFERENCE TO RELATED APPLICATIONS

This application claims the benefit of, and relies on the filing date of U.S. Provisional Application No. 62/200,464, filed on 3 Aug. 2015, the entire disclosure of which is incorporated herein by reference.

STATEMENT OF GOVERNMENT INTEREST

The present invention arose in part from research funded by the National Institute of Diabetes and Digestive and Kidney Disease (DK077064; DK077064-02S1) and the National Institute of Allergy and Infectious Diseases (AI094033-02). The U.S. Government has certain rights in this invention.

SEQUENCE LISTING

The instant application contains a Sequence Listing which has been submitted electronically in ASCII format and is hereby incorporated by reference in its entirety. Said ASCII copy, created on Oct. 20, 2016, is named 0184.0030-US_ST25 and is 2000 bytes in size.

BACKGROUND

The enteric nervous system (ENS) is a part of the peripheral nervous system (PNS) that operates largely independently of the central nervous system (CNS) to coordinate the complex behaviors of the gastrointestinal (GI) tract. ENS abnormality or dysfunction can lead to dysmotility syndromes include achalasia, gastro-esophageal reflux disease, delayed emptying of the stomach, abdominal pain and bloating, diarrhea and constipation [1]. Besides congenital motility disorders of ENS [eg Hirschsprung disease (HSCR) [2]], neuron degeneration also occurs in a large number of other diseases or pathophysiological conditions, such as diabetic gastroparesis, intestinal pseudo-obstruction of motility, and age-related neuronal loss in ENS [3]. Remarkably, recent reports have shown that lesions in ENS occur at very early stages of these diseases, even before the involvement of the central nerve system [4]. So far, however, no effective therapy is available for these syndromes or disorders, and thus new and effective treatments are urgently needed [1,3,5].

Advances in stem cell research over the past two decades have opened up the possibility of using stem cells to treat neuron injury or degeneration diseases [6,7,8]. Multiple types of stem cells, including embryonic stem cells (ESC) [9], ESC-derived neural precursors [10], induced pluripotent stem cells (iPSC) [11], neural stem cells [12], neural crest-derived stem cell [13] and enteric nervous system stem cells [14,15], have been demonstrated to be capable of being converted to neural and glial lineage [6,7,16,17].

Adult bone marrow-derived mesenchymal stem cells (BMSCs) are multipotent progenitors that are capable of osteogenic, adipogenic and chondrogenic differentiation, as well as displaying transdifferentiation potential beyond the mesenchymal lineages, including differentiation into neurons (although this remains controversial) [18,19,20,21,22, 23]. In addition, due to their active expansion capacity, high plasticity, and especially their low immunogenicity, BMSCs remain as unique and attractive candidates for allogenic cell-replacement therapies [23, 24A and 24B]. By December 2013, there had been 347 registered clinical trials using mesenchymal stem/stromal cells, according to "Clinicaltrials.gov registry on Dec. 15, 2013" [See also 24B, especially FIG. 1].

Functional improvement through BMSC therapy has been reported in animal models of CNS injury, such as traumatic brain injury or spinal cord injury et al [8,25,26,27,28,29]. While some of the underlying mechanisms have been well documented, others are controversial or being challenged or poorly understood, including involvements of direct-transdifferentiation of BMSCs into neurons, spontaneous cell fusion, anti-inflammatory property and modulation of neurotrophic mediator [18,19,30,31,32]. In addition, it is unclear how BMSCs take part in ENS circuit repair [33].

The properties and clinical applications of BMSC have always been a focus of debate since data from different reports are not always consistent, most likely due to the lack of disease-specific standardization or less-than-optimal experimental conditions [18,19,20,21]. For these reasons, MSC researchers have made significant efforts, by modulating microenvironments of MSCs ("reconditioning" or "reprogramming" of MSC) before and after transplantation, on improving therapeutic potential and consistency [37,38, 39]. Nevertheless, there remains a desire in the art to develop BMSC populations, which may used to treat ENS-related disorders.

BRIEF DESCRIPTION OF THE DRAWINGS

The patent or application file contains at last one drawing executed in color. Copies of this patent or patent application publication with color drawing(s) will be provided by the Office upon request and payment of the necessary fee.

The present invention will become more fully understood from the detailed description and the accompanying drawings, wherein:

FIGS. 1A-1I. In vitro preconditioned BMSCs exhibited a PGP9.5/Tuj1/HuC/D/nNOS-positive neuron-like phenotype (FIGS. 1A-1D). Cells were immunostained with neuronal marker (PGP9.5, NSE, Tuj1, HuC/D) and nNOS (colored panels). Images were obtained by fluorescent microscopy. Preconditioned cells expressed multiple neuronal markers [PGP9.5, NSE, Tuj1, HuC/D and nNOS]. Negative control (NC) in the presence of 2nd antibody (but absence of primary antibodies) showed no immunoreactivity. Nuclei were stained with DAPI (Blue). The far-right image of each colored panel is the overlay of the three images to its left. Representative of 5 independent experiments are shown (FIGS. 1E-1I). The percentage of positivity of PGP9.5, NSE, Tuj1, HuC/D and nNOS in preconditioned BMSC were shown individually as bar graphs in the panel. Cells were counted in at least 20 fields (10×) from each independent experiment (n=5).

FIGS. 2A-2C. Benzalkonium chloride (BAC) (0.5%) effectively ablated ENS in pylorus which remained essentially neuron-free for at least 28 days. (FIG. 2A) A schematic illustration of region of interest (ROI) in rat ENS denervation model. (FIG. 2B) Representative micrographs showing the immunoreactivity of neuron marker, PGP9.5, in 0.5% BAC treated group (right) and sham-operated group (left). (FIG. 2C) PGP9.5 levels in pylorus at day 28 examined by Western blot analysis with sham operation as control. Upper panel, representative Western blots; lower panel, statistical analysis of PGP9.5 expression (n=4-6). Data are shown as mean±SEM. *P<0.01. IHC (upper panel) and IF (lower panel).

FIGS. 3A-3H. Allogenically transplanted BMSC can survive in specific niches of pyloric wall and promote de novo regeneration of neuron-like cells/structures (which were not originated from grafted BMSCs). (FIG. 3A) Preconditioned BBM-labeled BMSC remained in the subserosal layer (where they were injected) one day after transplantation (FIG. 3A, left panel, blue, right panel, SHAM). Most of the transplanted BMSC migrated from serosal side to the longitudinal/circular muscle layer 7 days after transplantation (3A, middle panel, blue). [M, mucosal layer; SM, submucosal layer; LM, longitudinal muscle layer; CM, circular muscle layer; S, serosal layer]. FIGS. 3B-3H Transplanted BMSC promoted de novo regeneration of new neurons. At 28 day post-transplantation, most grafted BMSC migrated to the submucosal layer (SM), and survived, in the absence of any immunosuppressive agent or caspase inhibitor (FIG. 3B, blue). Most of grafted BMSC maintained strong PGP9.5-positivity in SM (FIGS. 3E-3G, SM, pink). A very small fraction of grafted BMSC were PGP9.5-negative and closely located in mucosa (FIGS. E-F, M, blue). A large quantity of regenerated PGP9.5-positive neurons was detected in predominantly muscle layer (and some in submucosa) (FIG. 3C, red larger structures). Merged image show these regenerated neuron-like cells/structures (FIG. 3E, red) had not originated from grafted BMSC because no blue color (BBM) was detected in any of these new neurons 8 see enlarged images (FIGS. 3F, 3G, 3H) of the areas marked with green rectangles (FIG. 3E).

(FIGS. 4A-4C) New neurons (in red, larger structures) exhibit strong expression of HuC/D FIG. 4A, Tuj1 (FIG. 4B), and nNOS (FIG. 4C), as compared to grafted BMSC [in blue or pink (overlay), smaller structures]. Representative from 15 rats are shown. (FIG. 4D) The regenerated PGP9.5-positive neuronal structures in the muscular layer are less ordered compared with that of normal control rats (sham controls with no BAC treatment). FIG. 4E. Western blot analysis demonstrated dramatic increase of various neuronal markers (also shown in the immunohistology in (FIG. 4A) in pyloric wall of BMSC-grafted denervated rats. Quantitative analysis of Western blots (FIG. 4E, lower panel) by densitometry (normalized to β-actin graph), using one-tailed Student's t-test. Error bars denote SEM. *P<0.01. Representative of at least 5 independent experiments are shown. Scale bar, 100 μm.

FIGS. 5A-5D. Regenerated neurons and neuronal structures do not originate from grafted in vitro preconditioned GFP-BMSC. 28 days post transplantation, BMSCs from in vitro-preconditioned GFP-transgenic mice were detected in pyloric wall (GFP; green). The regenerated neuron-like structures (PGP9.5; red) did not colocalize with grafted GFP-BMSC. Representative images from the examination of 3 rats transplanted with GFP-BMSC, as well as 5 sham normal control rats. Scale bar, 100 μm.

(FIG. 6A) Representative basal curves of isometric tension of circular pylorus muscle strips isolated from BAC-ablated group (lower panel), sham operation group (middle panel), and BMSC+ BAC-treated group (upper panel). (FIG. 6B) The tension (analyzed as grams and normalized for the cross-sectional area of the strip (g/mm2) of each treatment group is expressed as mean±SEM under both basal. (FIG. 6C) Representative traces of neural response induced by electrical field stimulation of circular pylorus strips at increasing frequency of stimulation (1-8 HZ) under NANC conditions (5 μM atropine and 3 μM guanethidine) from BAC-ablated group, BMSC+BAC-treated group and sham operation group. (FIG. 6D) Quantification of circular pylorus strip relaxations in response to EFS under NANC conditions in BAC-ablated group, BAC-ablated followed by BMSC treatment group and sham operation group. One-way ANOVA showed significant differences between the BAC-ablated group and BMSC treatment group at all stimulation frequencies. *P<0.05, **: P<0.01. Results are mean±SEM. of 8-11 strip preparations. (FIG. 6E) Quantitative analysis of L-NAME effect (300 μmol/L) on NANC-induced relaxations of pylorous muscle strips from the three experimental groups in response to EFS. Results are mean±SEM. of 8-11 strip preparations.

FIG. 7A GDNF, which was expressed at a very low level endogenously in BMSCs, was dramatically enhanced by in vitro GDNF induction. The relative expression of GDNF RNA was examined by real time PCR. FIG. 7B 28 days after BMSC transplantation, a continuous, stable high level of GDNF expression was detected in denervated pyloric wall, comparing with sham injected group (upper panel). Relative GDNF level was normalized with β-actin (lower panel). *P<0.01. Data was shown as mean±SEM, and are representative of at least 3 independent experiments.

FIGS. 8A-8F. Typical morphology of BMSC primary culture at different passages (P0, P2, P4, P6) were shown: The first week after seeding passage 0 (P0) [Day 1 (FIG. 8A); Day 3 (FIG. 8B); Day 7 (FIG. 8C); P2 (FIG. 8D), P4 (FIG. 8E) and P6 (FIG. 8F). At P6, most of BMSC were spindle-shaped and formed as whirling pattern when grown to confluence. (FIG. 8G). Detection of CD90/CD73/CD105/CD45 of cultured bone marrow stromal cells by flow cytometry. CD90/CD73/CD105-positive and CD45-negative suggests that cultured BMSC are highly homogeneous. (FIG. 8H) The expression of PGP9.5 and nNOS were barely detectable in unconditioned BMSCs. Data was representative of at least 3 independent experiments.

FIG. 9A-9C. In vitro adipogenic and osteogenic differentiation of BMSCs. The adipogenic, osteogenic and chondrocyte differentiation assays were performed using a kit from Cyagen Biosciences according to manufacturer's instructions. Representative images of three typical types of BMSC differentiations were shown, including adipocytes (FIG. 9A); stained with oil red), osteoblasts (FIG. 9B); stained with alizarin red), and chondrocytes (FIG. 9C); stained with alcian blue). Representative of at least three replicating experiments for each cell-type differentiation is shown.

FIGS. 10A-10H. 0.5% BAC is necessary to establish ENS-denervation model in pylorus of rats. (FIGS. 10A-D). Three doses of BAC, including 0.1% 0.3% and 0.5%, were tested for optimal concentration of establishing denervation model in rat pylorus. Expression of neuron marker, protein gene product 9.5 (PGP9.5) localized in mesenteric plexus was examined by immunohistology 28 days post-BAC treatment or sham operation as described in methods. 28 days after 0.1% and 0.3% BAC treatment in pylorus of rats, PGP9.5 positive neurons were still detectable, although dramatically decreased when compared with those in sham operation group. In the pylorus of mice treated with 0.5% BAC, no enteric nerves were detected. Thus 0.5% of BAC was used to establish the pylorus denervation model. (FIGS. 10E-H). The images of PGP9.5 IHC in both sham operation and BAC-treated group with higher magnification were shown. Photographs show representative results of PGP9.5 IHC (n=4-6).

FIGS. 11A-11G. Unconditioned BMSC do not induce de novo neuron regeneration. Grafted BMSC were predominantly localized in the submucosal layer 28 days after transplantation (only small number in mucosa and muscle layer) [FIG. 11A, FIG. 11D, as well as FIG. 11E and FIG. 11G (an enlarged area of FIG. 11A and FIG. 11D, respectively, marked by the green boxes); blue)]. No newly regenerated PGP9.5-positive neurons were observed in pyloric wall 28 days after unconditioned BMSC transplantation [PGP9.5; FIG. 11B, and FIG. 11F (an enlarged area of FIG. 11B); red]. Note: Panels FIG. 11A, FIG. 11B, FIG. 11C, and FIG. 11D are images of a same area, showing BBM-labeled BMSC (FIG. 11A), PGP9.5 expression (FIG. 11B), morphological structure by light microscopy (FIG. 11C), and the overlay image of FIG. 11A and FIG. 11B (FIG. 11D); FIG. G is the overlay image of FIG. E and FIG. F. M, mucosa; SM, submucosa; CM/LM, circular/longitudinal muscle).

BRIEF SUMMARY

Figure 3A:
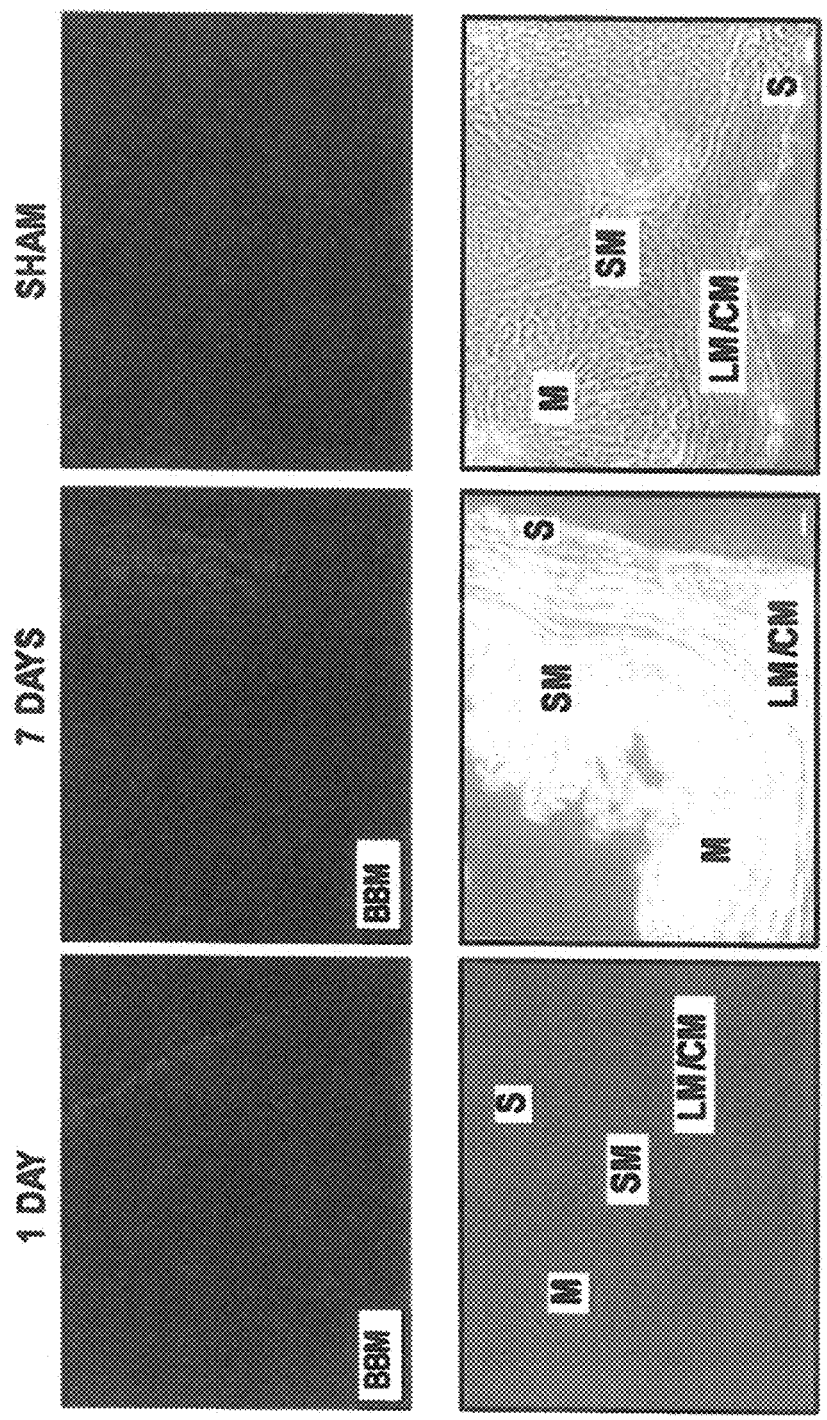

The present disclosure provides a composition including: an isolated in vitro pre-conditioned population of adult bone marrow derived mesenchymal stem cells (BMSCs), wherein the BMSCs express neuronal markers, and wherein the neuronal markers are PGP9.5, NSE, Tuj1, HuC/D, and neuronal nitric oxide synthase (nNOS).

Also provided herein is a method of treating an enteric nervous system-related disorder including: administering to a subject in need thereof a pharmaceutical composition including an isolated in vitro pre-conditioned population of adult bone marrow derived mesenchymal stem cells (BMSCs), wherein the BMSCs express at least one neuronal marker, and wherein the at least one neuronal marker is PGP9.5, NSE, Tuj1, HuC/D or neuronal nitric oxide synthase (nNOS) and a pharmaceutically acceptable carrier.

The disclosure further provides a method of preparing mesenchymal stem cells exhibiting a neuronal-like phenotype which method includes: isolating adult mesenchymal stem cells from a bone marrow; culturing the adult mesenchymal stem cells in a medium including glial cell derived neurotrophic factor and a fetal gut culture medium, wherein the cultured mesenchymal stem cells express at least one marker of PGP9.5, NSE, Tuj1, HuC/D or nNOS, thereby providing mesenchymal stem cells exhibiting a neuronal-like phenotype.

DETAILED DESCRIPTION

The following description of the embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present disclosure provides in vitro pre-conditioned bone-marrow derived mesenchymal stem cells (BMSCs) as described herein, which exhibit a neuronal-like phenotype. The present inventors have surprisingly found that the instant BMSCs are capable of effectively inducing regeneration of enteric neurons and restoring defective gastric contractility. Accordingly, the present BMSCs may be used to treat dysmotility syndrome and neuron degeneration in the gastrointentestinal tract, for example, as described herein below.

Compositions

As noted above, the present disclosure provides adult mesenchymal stem cells derived from bone marrow (BMSCs), which are pre-conditioned in vitro. As used herein "stem cells" refer to undifferentiated cells without mature tissue-specific characteristics, characterized by a capacity to either proliferate indefinitely (self-renewal) or to originate tissue specific committed progenitors or differentiated cells. "Mesenchymal Stem Cells" are multipotent stromal cells that can differentiate into a variety of cell types, including: osteoblasts (bone cells), chondrocytes (cartilage cells), myocytes (muscle cells) and adipocytes (fat cells) or as described herein, neuronal-like cells.

The BMSCs used in the present compositions and methods may be fresh, frozen, or have been subject to prior culture. In some embodiments, the BMSCs are mammalian cells, including human and non-human primates, domestic animals and livestock, pet or sports animals, for example, dogs, horses, cats, sheep, pigs, and cows. Typically, however, the BMSCs are human cells.

In some embodiments, BMSCs are obtained from bone marrow, such as from femur bone marrow, using protocols familiar to one of ordinary skill in the art. See e.g. Pittenger et al. (1999) *Science* 284(5411):143-147; Liechty et al. (2000) *Nature Medicine* 6:1282-1286), which are herein incorporated by reference in their entireties.

In some embodiments, the BMSCs are separated from other cells in the bone marrow, such as hematopoietic cells, by plating the isolated the cells on treated polystyrene tissue culture dishes. This allows the BMSCs to attach, while the hematopoietic or other cells remain in suspension, floating in the dish. The isolation media may be aspirated between about 0 to about 24 hours later, and immediately replaced with fresh isolation media, e.g., modified eagle medium containing 1,000 mg/L glucose, 15% fetal bovine serum (FBS), 2 mM glutamine, 100 U/ml penicillin and 100 µg/ml streptomycin. The cells may be serially passaged 2 or more times to ensure complete removal of any contaminating cells. Just prior to reaching confluence, the cells may be subcultured by first washing cells with a sterile solution, e.g., phosphate-buffered saline (PBS), followed by the addition of a solution comprising trypsin. Such subculturing allows maintenance of BMSC in culture for at least 10-20 passages.

The phrase "in vitro pre-conditioned" as used herein means that the BMSCs are cultured e.g., on a polystyrene tissue culture dish, in a medium that induces their differentiation into neuronal-like cells, e.g. the BMSCs express one or more neural markers. In various embodiments, the neural markers include, but are not limited PGP9.5, NSE, Tuj1, HuC/D, and neuronal nitric oxide synthase (nNOS).

In some embodiments, in vitro pre-conditioning is commenced after the BMSCs exhibit a distinct spindle shaped morphology and/or are positive for BMSC surface antigens CD90, CD73, CD105 while negative for hematopoietic cell marker CD45, e.g., after passage 6.

In some embodiments, the in vitro pre-conditioning occurs in a medium, such as Dulbecco's Modified Eagle's Medium (DMEM), containing growth factors, e.g., glial cell derived neurotrophic factor (GDNF) in fetal gut culture medium (FGCM). The FGCM may be prepared by any method known in the art [e.g., 40, which is herein incorporated by reference in its entirety] or as described in the examples. Briefly, in some embodiments, FGCM may be prepared by dissecting the guts from a mammal, such as embryonic rats, washed with $Ca^{2+}$- and $Mg^{2+}$-free PBS, incubated with a dispase/collagenase mixture and plated onto fibronectin-coated dishes in DMEM. The cell culture medium is then collected and the pH of the collected medium adjusted to be about pH 7.4 resulting in the FGCM.

In various embodiments, the cells are incubated in the medium containing, for example, GDNF and FGCM for a period of time, e.g. 10 days, after which neuronal markers are detectable. See Examples. The neuronal markers may be detected by any art known method including using labeled antibodies against the markers as described in the Examples.

In some embodiments, the population of in vitro pre-conditioned BMSCs prepared as described herein result in a cell population, wherein at least about 60%, at least about 70%, at least about 75% or at least about 80% of the in vitro pre-conditioned BMSCs express at least one neuronal marker. For example, in some embodiments, about 80% of the cells in the in vitro pre-conditioned BMSC population express PGP9.5, about 80% of the in vitro pre-conditioned cells in the BMSC population express NSE, about 75% of the in vitro pre-conditioned cells in the BMSC population express Tuj1, about 73% of the in vitro pre-conditioned cells in the BMSC population express HuC/D and about 78% of the in vitro pre-conditioned cells express nNOS.

Populations of in vitro pre-conditioned BMSCs can be formulated into pharmaceutical compositions for use in vivo. Such pharmaceutical compositions comprise a population of BMSCs in a pharmaceutically-acceptable carrier, e.g., a saline solution or other accepted physiologically-acceptable solution for in vivo administration. In various embodiments, the cells are able to maintain the neuronal like phenotype as described herein when administered in vivo for at least about one week, at least about 28 days or at least about 50 days.

In some embodiments, the in vitro pre-conditioned BMSCs are labeled with a bio-imaging agent to track, for example, the migration of the cells upon transplantation of the BMSCs into an organism. In some embodiments, bio-imaging agents are introduced into the cells or onto the cell surfaces before administration to an organism. For example, in vitro pre-conditioned BMSCs may be labeled with art-known fluorescent probes, e.g., 4',6-diamidino-2-phenylindole, for optical imaging, superparamagnetic iron oxide (SPIO) for MRI, and radiotracers for radionuclide imaging. Other well-known bio-imaging agents are described, for example, in Fu et al. *Expert Rev Cardiovasc Ther.* 2010 August; 8(8): 1149-1160, which is herein incorporated by reference in its entirety.

Methods

The present disclosure also provides a method of treating an enteric nervous system-related disorder (ENS), which includes injuries thereof and neurodegenerative disorders that extend to the enteric nervous system and which cause gastrointestinal dysfunction, by administering the in vitro pre-conditioned BMSCs to a subject in need thereof. As is well known in the art, the enteric nervous system (ENS) is the intrinsic nervous system of the gastrointestinal tract. The ENS contains complete reflex circuits that detect the physiological condition of the gastrointestinal tract, integrates information about the state of the gastrointestinal tract, and provide outputs to control gut movement, fluid exchange between the gut and its lumen, and local blood flow.

In some embodiments, the enteric nervous system disorder to be treated with the in vitro pre-conditioned BMSCs of the present disclosure is dysmotility syndrome. Dysmotility syndrome may involve any part of the gastrointestinal tract and may be caused by the nerves controlling the muscles. Dysmotility syndrome can be mild, moderate or severe. In some embodiments, dysmotility syndrome is characterized by an inability of food to move normally through the stomach and intestines (achalasia), gastro-esophageal reflux disease, delayed emptying of the stomach, abdominal pain, bloating, diarrhea and/or constipation. Dysmotility syndrome may include congenital conditions such as Hirschsprung disease.

In some embodiments, the enteric nervous system disorder to be treated with the in vitro pre-conditioned BMSCs of the present disclosure is gastroparesis. The term "gastroparesis" refers to a disorder that, e.g., slows or stops the movement of food from the stomach to the small intestine. Normally, the muscles of the stomach, which are controlled by the vagus nerve, contract to break up food and move it through the gastrointestinal (GI) tract. Gastroparesis can occur, for example, when the vagus nerve is damaged by illness or injury, causing the stomach muscles stop working normally. In subjects with gastroparesis, food can move slowly from the stomach to the small intestine or may stop moving altogether. In some embodiments, the gastroparesis is associated with diabetes.

In other embodiments, the enteric nervous system-related disorders to be treated using the instant methods include, but are not limited to a physical injury of any part of the gastrointestinal tract due to trauma, surgery or ischemia and necrotizing enterocolitis (NEC) [N Engl J Med 2011, 364: 255-264, which is incorporated by reference in its entirety).

In yet other embodiments, the enteric nervous system-related disorders include loss of enteric neurons due to aging and laxative use [3, 4, which are herein incorporated by reference in their entireties].

In yet still other embodiments, the enteric nervous system-related disorders include neurodegenerative disorders, such as Parkinson's disease (PD), which extends to the enteric nerve system [Neurology, 2011, 77 (19): 1761-7, which is herein incorporated by reference in its entirety].

The in vitro pre-conditioned BMSCs may be administered to a subject in need thereof in an amount effective to treat the enteric nervous system disorder, which can be readily determined by an ordinary artisan. Further, the in vitro pre-conditioned BMSCs may be administered by any method known in the art. For example, the in vitro pre-conditioned BMSCs can be administered by injection into a target site of a subject, typically via a delivery device, such as a tube, e.g., catheter. More typically, the tube additionally contains a needle, e.g., a syringe, through which the cells can be introduced into the subject at a desired location. Specific, non-limiting examples of administering cells to subjects may also include administration by subcutaneous injection, intramuscular injection, or intravenous injection. If administration is intravenous, an injectible liquid suspension of cells can be prepared and administered by a continuous drip or as a bolus. Cells may also be inserted into a delivery device, e.g., a syringe, in different forms. For example, the cells can be suspended in a pharmaceutically acceptable carrier as described above contained in the delivery device.

Typically, the cells are administered locally (for example by direct application under visualization during surgery). More typically, non-surgical and/or non-invasive administration is used. For instance, a conventional controllable endoscopic delivery device can be used so long as the needle lumen or bore is of sufficient diameter (e.g. 30 gauge or larger) that shear forces will not damage the cells being delivered. The in vitro pre-conditioned BMSCs may be administered in a manner that permits them to graft to the intended target site and induce the regeneration of neurons in the functionally deficient area.

In some embodiments, the target site to which the BMSCs are administered is a portion of the gastrointestinal tract. For example, the in vitro pre-conditioned BMSCs may be introduced into the esophagus, stomach, duodenum, small intestine or large intestine. More typically, the in vitro pre-conditioned BMSCs are introduced into the pylorus of the stomach. The in vitro pre-conditioned BMSCs may be introduced into any tissue layer of the gastrointestinal wall, e.g., mucosa, submucosa, serosa, subserosa or muscular layer (circular or longitundinal). Most typically, the target site for the in vitro pre-conditioned BMSCs is the submucosa.

In some embodiments the in vitro pre-conditioned BMSCs migrate after administration to a target site. For example, the in vitro pre-conditioned BMSCs may be administered to a subserosal layer of the pylorus of the stomach and then subsequently migrate to the submucosal region of the pylorus.

The subject to which the in vitro pre-conditioned BMSCs are administered may be a mammal, including human and non-human primates, domestic animals and livestock, pet or sports animals, for example, dogs, horses, cats, sheep, pigs, and cows. Typically, however, the subject is a human subject. The in vitro pre-conditioned BMSCs may be from the subject's own body (autologous transplant) or from a donor (allogeneic transplant).

Without being limited by theory, it is hypothesized that the regenerated neurons do not originate from the grafted in vitro pre-conditioned BMSCs, themselves, instead, the gastric neuron regeneration is induced by the in vitro pre-conditioned BMSCs but not from direct BMSC transdifferentiation.

The present disclosure is also directed to a method of preparing mesenchymal stem cells exhibiting a neuronal-like phenotype which method includes isolating mesenchymal stem cells from a bone marrow; culturing the mesenchymal stem cells, typically mammalian cells, such as human cells, in a medium including glial cell derived neurotrophic factor and a fetal gut culture medium, wherein the cultured mesenchymal stem cells express at least one marker e.g., PGP9.5, NSE, Tuj1, HuC/D or nNOS, thereby providing mesenchymal stem cells exhibiting a neuronal-like phenotype. The mesenchymal stem cells are isolated and cultured as described herein for in vitro pre-conditioned BMSCs. The properties of the mesenchymal stem cells cultured as described herein are capable of maintaining the neuronal like phenotype in vivo for a period of time as described above, typically 28 days. Further, the preparation method results in a population of in vitro pre-conditioned BMSCs having a distribution of neuronal markers as also described, e.g. typically about 80% of the bone marrow derived mesenchymal stem cells express PGP9.5, about 80% of bone marrow derived mesenchymal stem cells express NSE, about 75% of the bone marrow derived mesenchymal stem cells express Tuj1 and about 73% of the bone marrow derived mesenchymal stem cells express HuC/D and about 78% of the in vitro pre-conditioned cells express nNOS.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

EXAMPLES

Example 1: Materials and Methods

1(a). Animal.

Adult Sprague-Dawley rats (SD rats; 10-12 week old), either WT or GFP transgenic), were used in this study. Animals were maintained and used in accordance with NIH guidelines. Animal study protocols were approved by the Animal Care and Use Committee (ACUC) at the Johns Hopkins University and Huazhong University of Science & Technology (HUST). Animals were maintained in either the BRB Animal Facility at the Johns Hopkins University School of Medicine or in the Experiment Animal Facility of HUST, under controlled temperature (25° C.) and photoperiods (12 h:12 h light-dark cycle). Adult male WT or GFP rats (10-12 week old) were used as donors of BMSC. The adult female SD rats were used to establish the pyloric denervation model and also as recipients of BMSC transplantation.

1(b)(i) Preparation and Characterization of BMSCs.

BMSCs isolated from femurs were cultured in modified eagle medium (MEM) containing a lower concentration of glucose (1,000 mg/L), 15% fetal bovine serum (FBS), 2 mM glutamine, 100 U/ml penicillin and 100 µg/ml streptomycin. 24 hours after plating, non-adherent cells were removed by replacing the medium. The BMSC were split (0.25% trypsin/1 mM EDTA) and further enriched by passage cultures. BMSC at passage 6 were stained with antibodies to CD73, CD90, CD105 and CD45 (eBioscience, San Diego, Calif., USA) and characterized by FACS analyses.

1(b)(II) FACS Analyses.

BMSC at passage 6 were detached with 0.25% trypsin and 1 mmol/l EDTA, washed twice with PBS, and suspended with PBS (106/100 ul). Cells were incubated with phycoerythrin (PE)-conjugated monoclonal antibody against rat CD90, CD45, CD103 and CD73 for 30 min on ice. Fluorescence activated cell sorting (FACS) analysis was performed after two final washes using a FACS Caliber cytometer [Becton Dickinson (BD) Immunocytometry Systems, San Jose, Calif., USA]. Mouse IgG was set up as a negative control.

1(c) In Vitro Adipogenic, Osteogenic and Chondrogenic Differentiation of BMSC.

The differentiation assays were performed according to manufacturer's instructions (Cyagen Biosciences Inc; Cat. No. RASMX-90031, RASMX-90021, RASMX-90042). After adipogenic and osteogenic differentiation, cells were fixed with 4% formaldehyde solution for 30 minutes and air-dried. The adipogenic cultures were stained with Oil Red O (Cyagen Biosciences Inc). The osteogenic cultures were stained with Alizarin Red S solution (Cyagen Biosciences Inc) for 3-5 min. Chondrogenic pellets were harvested after 21 days in chondrogenic differentiation medium (Cyagen Biosciences Inc). The formalin-fixed and paraffin-embedded chondrogenic pellet was sectioned and stained for Alcian blue. Blue staining indicates synthesis of proteoglycans by chondrocytes. Differentiation of BMSC was visualized under light microscope and photographed.

1(d) In Vitro Differentiation of BMSCs by Glial Cell-Derived Neurotrophic Factor (GDNF) in Fetal Gut Culture Medium (FGCM).

After passage 6, BMSCs exhibited a distinct spindle-shaped morphology and a continuous expansion potential in in vitro-culture (FIGS. 8A-8H). The BMSCs in P6 were first pre-induced with basic fibroblast growth factor (bFGF, 10 ng/ml) in DMEM medium for 24 hrs. For in vitro differentiation, the pre-induced BMSCs were incubated in DMEM medium containing GDNF (10 ng/ml) and FGCM for 10 days, with medium change every 3 days. The FGCM solution was prepared as described [40, herein incorporated by reference in its entirety] with modifications (see below). Controls were BMSCs that were cultured in DMEM only (no GDNF or FGCM). BMSCs cultured in the absence of GDNF and FGCM did not undergo differentiation. See below.

1(d)(i) Preparation of Fetal Gut Culture Media (FGCM).

The guts from 8-10 embryonic SD rats (E15) were dissected, washed twice with $Ca^{2+}$- and $Mg^{2+}$-free PBS, and incubated with 1 mg/ml dispase/collagenase mixture (Sigma, St Louis, Mo., USA) for 15 minutes at room temperature. The tissue was washed twice with PBS, triturated by repeated pipetting, and then plated onto fibronectin-coated dishes (20 µg/ml) in DMEM. After 3 days, the cell culture medium was collected by centrifugation (84 g for 5 min). The pH of the collected medium was adjusted to be equal to DMEM (pH=7.4), resulting in FGCM. The FGCM was used at a 1:1 dilution with DMEM for in vitro BMSC differentiation.

1(d)(ii) Immunocytochemical/Immunohistological Analysis.

For grafted BMSCs and in vivo-regenerated neurons or neuronal structures in the denervated pylorus: 28 days following BMSC transplantation, mice were anesthetized with sodium pentobarbitone (45 mg/kg intraperitoneally), transcardially perfused, and fixed with freshly prepared ice-cold 4% paraformaldehyde in 0.1 mol/l PBS (pH 7.4). The pylorus was removed and fixed in 4% paraformaldehyde, and cryoprotected by infiltration in 30% sucrose solution in PBS overnight at 4° C. The tissue was rapidly frozen in O.C.T embedding medium over dry ice-chilled isopentane. Frozen serial sections (7 µm) were cut on a cryostat, placed on gelatin-coated slides (protected from light). Frozen sections were blocked and permeabilized for 1 hour at room temperature with 0.1% Triton X-100 in PBS containing 15% normal goat serum. After washing in PBS, sections were incubated with primary antibodies diluted in PBS containing 1.5% normal goat serum overnight at 4° C. Antibodies used in the study include anti-protein gene product 9.5 (PGP9.5; rabbit), anti-nNOS (rabbit; Chemicon); anti-NSE (mouse; Abcam); anti-Tuj1 (chicken; Millipore); anti-HuC/D (mouse, Molecular Probes, Life Technologies). After washing, sections were incubated with Alex-conjugated goat anti-rabbit (or anti-mouse, or chicken) secondary antibodies (Invitrogen) for 1 hour at room temperature. Negative controls were processed in the same way except that no primary antibodies were used.

1(d)(iii) For Analyses of Unconditioned or In Vitro Pre-Conditioned BMSC:

Cells grown on cover slips were fixed with 3% paraformaldehyde. Cells were neutralized in PBS with glycine (20 mM) for 10 min and then permeabilized in 0.1% saponin in PBS for 20 minutes. After a 60-minute blocking step in 10% FBS and 1% BSA in PBS, cells were incubated with primary antibodies followed by second antibodies as described above for the in vivo immunostaining. Specimens were analyzed under LSM510 confocal microscope or IX70 Olympus microscope equipped for phase contrast and epi-fluorescence.

1(e) Establishment of Pyloric Denervation Model Using Benzalkonium Chloride (BAC).

The submucosal and myenteric plexus in rat pylorus were ablated using a myenterically and extrinsically denervated rat model [41,42, which are herein incorporated by reference in their entireties] with modifications. Rats were anesthetized with 45 mg/kg sodium pentobarbital and the pylorus was exteriorized through a 1-cm midline incision. Patches of gauze pre-absorbed in three different concentrations of BAC (0.1%, 0.3%, and 0.5%) were circularly applied, respectively, to the entire serosal surface of 3-cm segments that span the pyloric region for 20 minutes (1.5 cm each at proximal duodenum and distal antrum; see the schematic illustration in FIG. 2A). The 1-cm middle segment of the denervated area was defined as the regions of interests (ROI), as illustrated in FIG. 2A. All experimental analyses, including efficiency of denervation or BMSC-initiated regeneration, were restricted to the ROI. Sham control rats were treated identically except that the gauze was soaked with 0.9% saline (instead of BAC). The ROI specimens from BAC-treated and saline-treated sham-operation group were dissected at day 1, 7, and 28 post-transplantation, respectively (see below). There were 4-6 rats each group, including treatments with various concentrations of BAC or sham-operation.

1(f) Transplantation of BMSCs.

For transplantation, in vitro preconditioned PGP9.5-positive BMSC, or unconditioned PGP9.5-negative BMSC (controls) were fluorescently labeled by incubating with 1 µg/ml bis-benzimide (BBM; Hochest 33258, Sigma) for 24 hours. The BBM-labeling allows tracking the transplanted BMSC in vivo. Before transplantation, for the BMSCs labeled with BBM, cells were washed with DMEM three times to remove the excessive BBM. BMSCs generated from bone marrow of GFP-transgenic rats were also used as the second approach to track the BMSC after transplantation.

BMSC (BBM- or GFP-labeled) were prepared at a concentration of 10,000 cells/µl in Dulbecco's phosphate-buffered saline (PBS) and kept on ice. Three days post-BAC treated denervation, 50 µl of BMSC suspension was injected, twice (each on the opposite side of the pylorus) from serosal surface into the longitudinal smooth muscle of denervated pylorus using a 22-gauge needle attached to a 50-µl Hamilton syringe (a total of 1.0×106 cells were injected per rat). Same volume of DMEM was given in the same way to the sham operation group. The experimental BAC-treated rats were divided randomly into 4 groups: in vitro pre-conditioned BMSC transplantation group (n=15), sham operation group (n=15), unconditioned BMSC transplantation group (n=5), and in vitro pre-conditioned GFP-BMSC transplantation group (n=5).

1(g)(i) Measurement of Isometric Contractility.

Muscle strips isolated from pylorus containing the denervated zone were prepared as previously described [43, herein incorporated by reference in its entirety] and as below. Tension under basal condition and relaxation under electric field stimulation (EFS) condition were measured according to a previously described protocol [44, herein incorporated by reference in its entirety]. Results are mean±SEM from 8-11 strip preparations (from 8-11 rats) for each group.

1(g)(ii) Pyloric Functional Studies.

The stomach was opened from the great curvature and gently cleaned luminal contents with Krebs solution. The mucosal layers were removed using cotton tips under microscopic control. The 10-mm length and 6 mm width muscle strips were gently peeled off from pylorus in circular direction and kept in 25-ml warm (37° C.) organ baths containing oxygenated (95% $O_2$/5% $CO2$) Krebs solution. The muscle stripe was connected between an isometric force transducer (Fort-10, WPI, USA) and the armature of the bath. Tissues were preloaded with 1.0 g force, and allowed to equilibrate in the baths for 45 min until a stable baseline was obtained. Frequency spectra (1, 2, 4, 8 Hz) were obtained by pulse trains (pulse 1 ms, train 10 s, 15 V. Voltage was kept constant by using a Med Lab Stimu-Splitter II (Med Lab, Loveland, Colo., USA). Non-adrenergic, non-cholinergic (NANC) conditions were induced with 5 µM atropine and 3 µM guanethidine. NG-nitro-l-arginine methyl ester hydrochloride (L-NAME, 300 µm), obtained from Sigma (St Louis, Mo., USA), was used as a NOS inhibitor. Muscular tension was recorded by a polygraph (MP100, Biopac Systems Inc., USA); The neural response obtained in the presence of EFS was calculated as the mean response during (on-response) the stimulation period and was analyzed as grams and normalized for the cross-sectional area of the strip (g/mm2 with Biopac Acknowledge software (Biopac Systems, Inc., USA).

1(h)(i) Real-Time (RT)-PCR,

Western blotting and Immunohistological analysis were performed as previously described [45,46, which are herein incorporated by reference in their entireties], as well as below.

1(h)(ii) Analysis of GDNF mRNA Expression by Real-Time (RT)-PCR.

Total RNA was extracted from BMSC at passage #6 or tissues from ROI of adult rat pylorus by Trizol Reagent (Invitrogen). Reverse transcription was performed using MultiScribe™ Reverse Transcriptase Kit (ABI). Real time PCR of GDNF was performed using following primers: for GDNF RT-PCR, 5'-TGAAGTTATGGGATGTCGTGG-3' (SEQ ID NO: 1) and 5'-GCCGCTTGTTTATCTGGTGA-3' (SEQ ID NO: 2); and for β-actin (control), 5'-AGGGAAATCGTGCGTGAC-3' (SEQ ID NO: 3) and 5'-ACCCACGGAAGGAAGGCT-3' (SEQ ID NO: 4). In a sterile Eppendorf tube on ice, 7 µl ddH2O, 10 µl SYBR® Green Reagent, 1 µl GDNF or β-actin primers (10 pM) each, 1 µl cDNA were mixed (Total volume: 20 µl). After incubation at 95° C. for 10 min, the solution was cycled 40 times through a program of 15 s at 90° C., 1 min at 60° C. followed by 15 s at 95° C., 1 min at 60° C. and 15 s at 95° C. as melt curve stage.

1(h)(iii) SDS-PAGE and Western Blotting.

The expression of the following proteins, including neuron markers PGP9.5/NSE/HuC/D/Tuj1, neuronal transmitter nNOS, and neurotrophic factor GDNF in BMSC in vitro or pylorus denervated rats in vivo (with or without BMSC transplantation), were analyzed by SDS-PAGE and Western blot, which was performed as we previously described. For BMSC in vitro, cells with different treatments were washed twice in PBS, detached with ice-cold PBS, centrifuged and collected as described previously [3, herein incorporated by reference in its entirety]. For in vivo study of pylorus, tissues were homogenized using a Polytron homogenizer in the same lysis buffer described above. Proteins were separated by SDS-PAGE and transferred onto nitrocellulose membrane. Western blot analysis was performed as we previously described. The antibodies used for Western blot include anti-PGP9.5 and anti-nNOS (rabbit; Chemicon); anti-NSE (mouse; Abcam); anti-Tuj1 (chicken; Life Span BioScience); anti-GDNF and anti-β-actin (mouse; Santa Cruz Biotech). Proteins of interests were visualized on an Odyssey Infrared Imaging System (Li-Cor, Lincoln, Nebr.). The β-actin protein level was used as a protein loading control.

1(i) Statistical Analysis.

Quantitative expression of proteins/mRNAs of interests was calculated as the ratio of integrated optical density of protein or mRNA to that of β-actin. Quantification of mRNA or protein expression was calculated from at least 10 samples in three independent experiments. Results are shown as mean±SEM. All statistical analyses were carried out using SPSS software (Version 11.5; SPSS; Chicago, Ill., USA) with one-tailed Student's t-test. Statistical significance was set at $p<0.05$.

Example 2: Results

2(a) Generation of Highly Homogenous CD90/CD73/CD105-positive and CD45-negative Rat BMSC with Multipotent Differentiation Potential.

Figure 8A:
FIGS. 8A-8H. Isolated bone marrow-derived BMSC at passage 6 exhibit spindle-like shape and are high in purity (CD90/CD73/CD105-positive and CD45-negative).
Figure 8B:
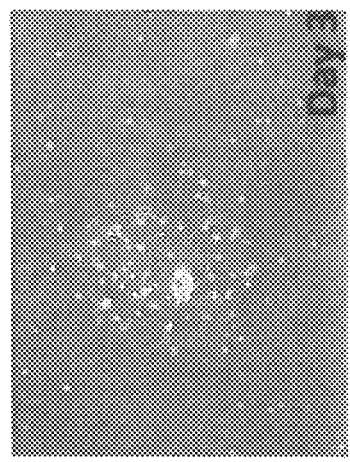
Figure 8C:
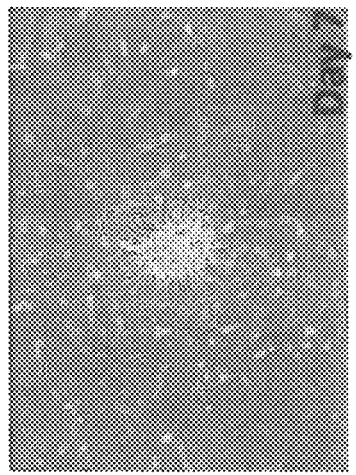
Figure 8D:
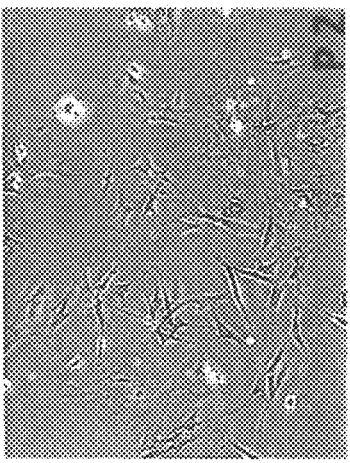
Figure 8E:
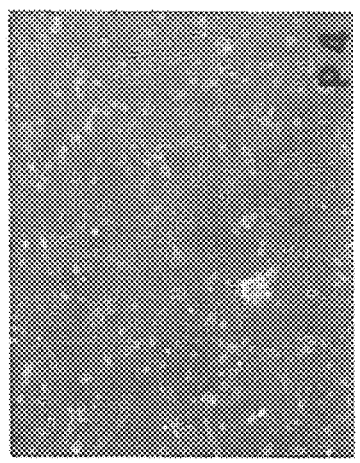
Figure 8F:
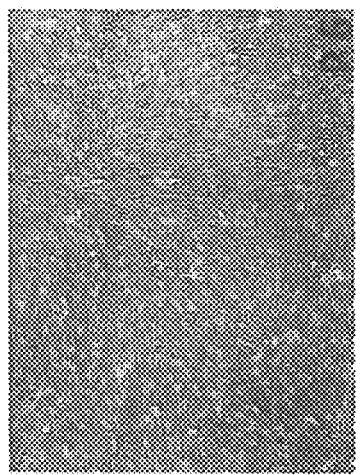
Figure 8G:
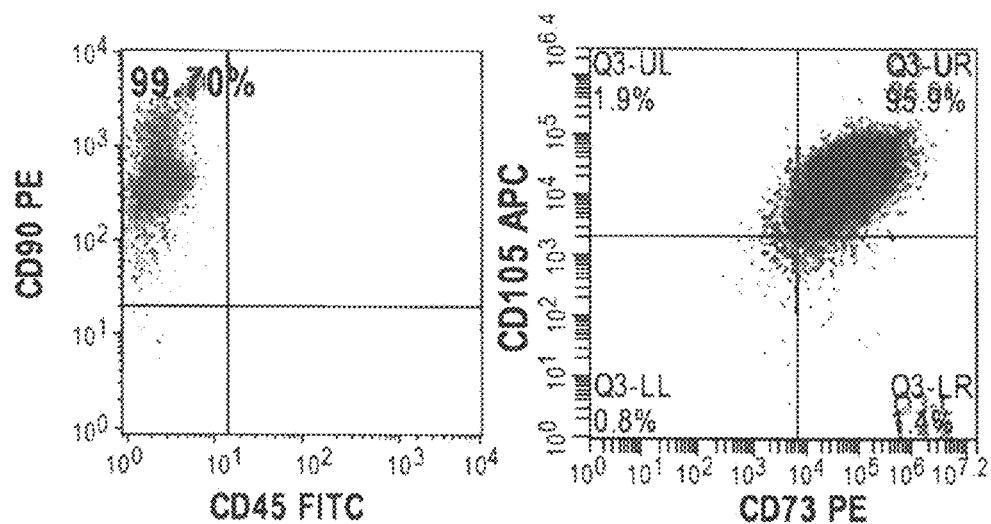

Bone marrow-derived adherent cells were isolated and cultured as described in the Methods, as reported previously [47, herein incorporated by reference in its entirety]. 24 hours after seeding, BMSC isolated from rat bone marrow adhered to the bottom of plastic flasks. The cells grew slowly as single colonies 3-7 days post-seeding FIGS. 8A-C. During P2 to P6, BMSC became characteristically spindle-shaped (FIGS. 8D-F). BMSCs were capable of efficient cell expansion for at least 20 passages (the most tested). Flow cytometry analysis of P6 demonstrated that the BMSC were positive with BMSC surface antigen CD90 (99.70%-positive), CD73, CD105 (95.9%-positive), while negative for hematopoietic cell marker CD45 (FIG. 8G) These cells are able to differentiate to osteoblasts, adipocytes and chondroblasts under standard in vitro differentiating conditions (FIGS. 9A-9C).

2(b) Isolated BMSC were Efficiently Preconditioned In Vitro into Neuron-like Cells in GDNF-containing Fetal Gut Culture Medium (FGCM).

Figure 8H:
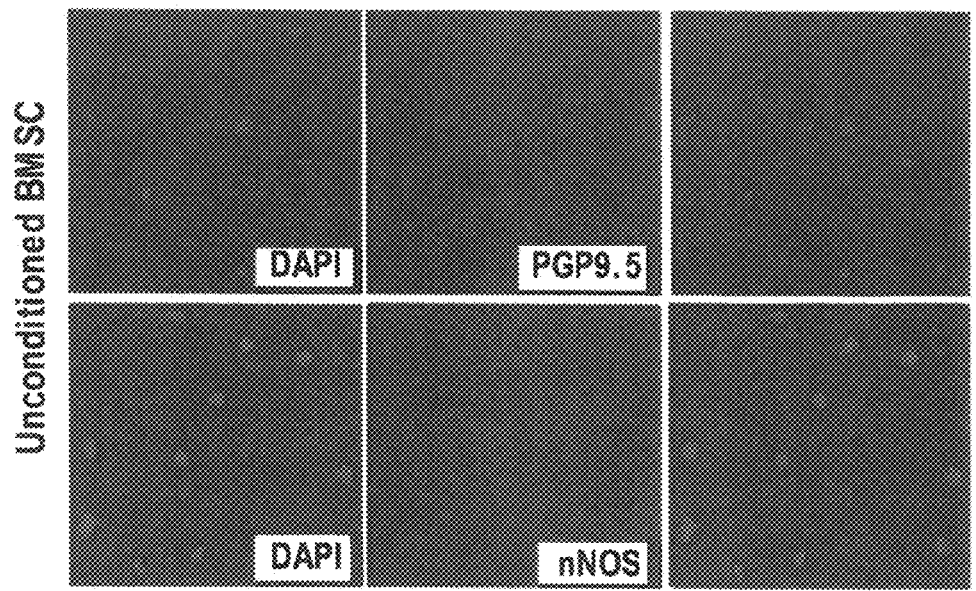
Figure 12C:
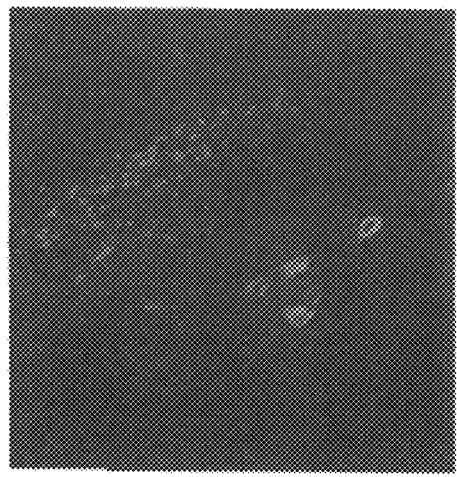
FIGS. 12A-12E. Regenerated neurons exhibit various morphologic features. Regenerated neurons or neuronal structures exhibit a variety of morphologies (FIGS. 12A-E). These regenerated neurons or neuronal structures of various shapes and sizes remain to be further characterized in the future studies. Scale bar, 100 µm.
Figure 12B:
Figure 12A:
Figure 12E:
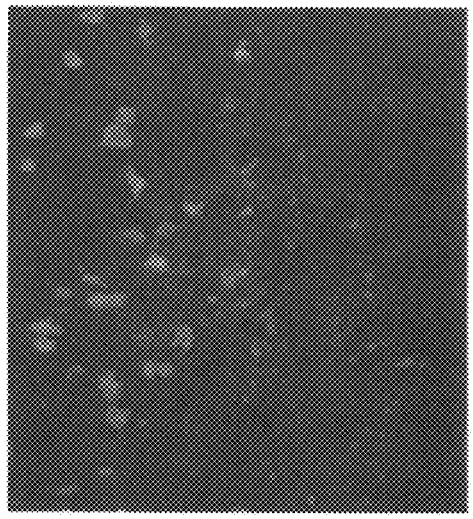
Figure 12D:

In order to differentiate the isolated BMSCs into a neuron-like phenotype (expressing multiple neuronal markers) prior to transplantation, isolated BMSC were pre-conditioned in vitro with basic fibroblast growth factor (bFGF) and glial cell line-derived neurotrophic factor (GDNF) in FGCM. The expression of PGP9.5 and neuronal nitric oxide synthase (nNOS) was essentially undetectable in unconditioned BMSC (FIG. 8H). However, the majority of the in vitro pre-conditioned BMSC abundantly expressed the well-established neuronal markers, including PGP9.5 (80.3±3.1%), NSE (79.3±10.3%), Tuj1 (75.1±8.2%) and HuC/D (72.7±7.4%). These data indicate that in vitro pre-conditioned BMSC exhibit a neuronal phenotype under the induction conditions (FIGS. 1A-1I). In addition, 78.3±5.3% of in vitro pre-conditioned BMSC also expressed nNOS. nNOS could produce nitric oxide, a major inhibitory neurotransmitter in the ENS. The expression of nNOS in these in vitro pre-conditioned BMSCs further indicates their "neuron-like" phenotype (FIGS. 1A-1D).

2(c) Higher Concentration of Benzalkonium Chloride (BAC) is Necessary for Denervation in Pylorus.

To ensure complete BAC-induced denervation, a region of interest (ROI, a 1 cm area in the middle of the 3 cm BAC-induced denervated region of pylorus), was studied (FIG. 2A). The pylorus was also used as an anatomical structure for transplanting BMSCs to the area where denervation occurred. Initial experiments were directed at determining the optimal dose of BAC (0.1%, 0.3%, 0.5%) for pylorus denervation as shown in FIG. 10A-10H. 28 days after 0.1% and 0.3% BAC treatment, PGP9.5 positive neurons were significantly reduced, but still detectable. However, in rats treated with 0.5% BAC, PGP9.5 positive neurons became undetectable with either immunofluorescence (IF) or immunohistochemistry (IHC) (FIG. 2B). These observations were further confirmed by Western blot analyses of PGP9.5 expression, which was markedly decreased (to an essentially undetectable level) in the ROI of pyloric wall after 0.5% BAC treatment (FIG. 2C (2.28±0.28 vs. 0.19±0.06; p<0.01)). The data indicate that application of a higher concentration BAC (0.5%) to a longer segment of pylorus (an additional 1 cm at each side of ROI) is sufficient to induce and maintain a virtually complete denervation in the ROI for at least 28 days (FIGS. 2A-2C and FIGS. 10A-10H).

2(d) Allogeneic In Vitro Pre-conditioned BMSC not Only Survive in the Niche of Pyloric Wall but also Maintain a Neuron-like Phenotype 28 Days after Transplantation.

To determine the success of BMSC transplantation and new nerve development, at various post-transplantation time points, the ROI of pyloric wall was dissected and then cut into serial sections and analyzed. Survivability and localization of grafted BMSCs, as well as the localization of new neurons were carefully examined and compared by a blinded observer. On day one, transplanted BMSCs, administered by sub-serosal injection, were observed only at the serosal or sub-serosal locations (FIG. 3A, left panel). 7 days after transplantation, most BMSCs had migrated to the longitudinal/circular muscle layer (FIG. 3A, middle panel). At day 28, transplanted cells had survived and accumulated predominantly in the submucosa (blue, FIG. 3B). It is clear that the density of grafted BMSCs (stained as blue color by BBM) had shifted their location from the serosal side toward the mucosal layer over time. Most transplanted cells retained their neuron phenotype (PGP9.5/Tuj1/HuC/D/nNOS-positive) as shown in FIG. 3E,G, the merged images of FIGS. 3B and C [purple or pinkish purple as the result of merging blue (BBM) and red (PGP9.5)]. Only a small number of grafted BMSCs exhibited PGP9.5-negative phenotype (blue color only in merged image, FIG. 3E,F). However, these negative cells were localized close to the mucosa layer, blue color FIG. 3D,E,F; blue color), but not that of the submucosa (FIG. 3D,E,G, blue).

2(e) Regenerated Myenteric Neuronal Structures do not Originate from Transplanted BMSCs.

Figure 4A:
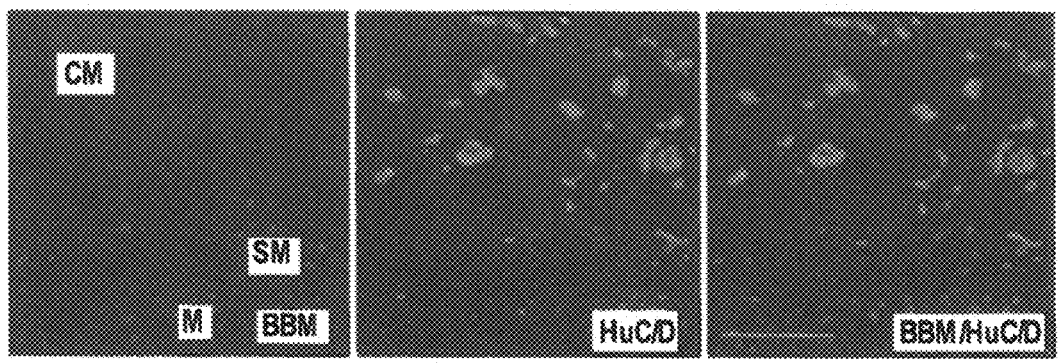
FIGS. 4A-4E. The regenerated neurons induced by BMSC were positive for multiple neuron markers and mutually exclusive with grafted BMSC.
Figure 4B:
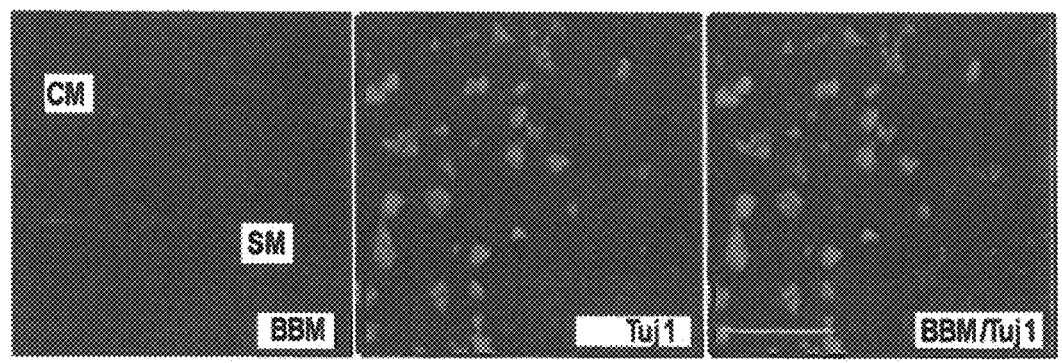
Figure 4C:
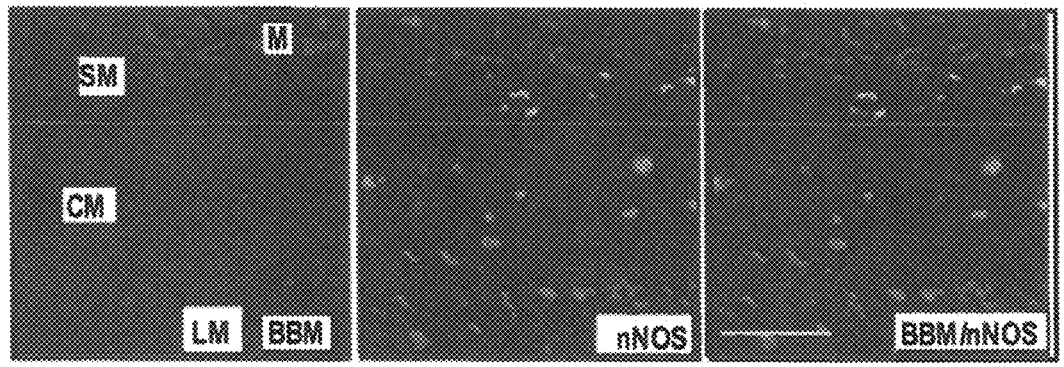
Figure 4D:
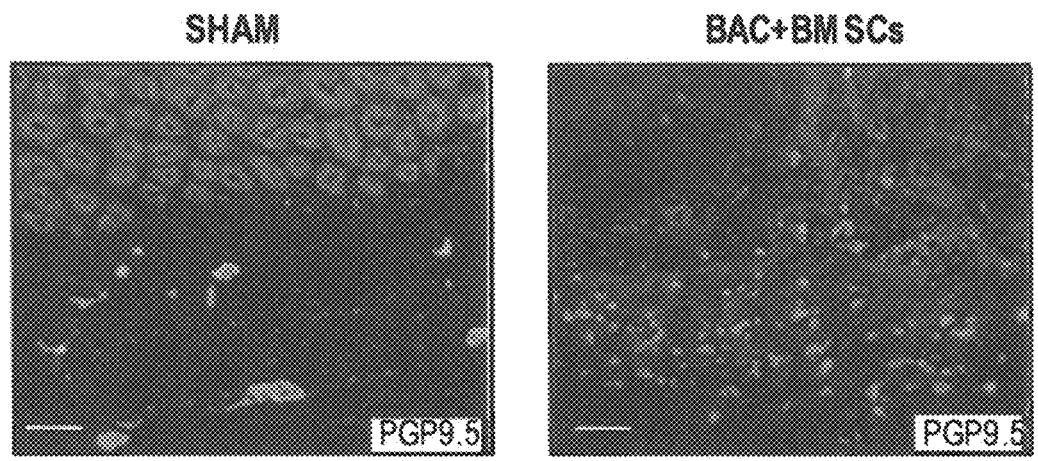

28 days after transplantation of in vitro pre-conditioned BMSCs, a massive number of new neurons or neuronal structures were regenerated in each rat (FIGS. 3B-3H and FIGS. 4A-4C, red). This did not occur in rats transplanted with unconditioned BMSCs FIGS. 11A-11G. These regenerated neuronal structures exhibited multiple neuronal markers, including PGP9.5, Tuj1, HuC/D and nNOS (immunohistology: FIGS. 3B-3H, FIGS. 4A-4C and FIGS. 5A-5D, red; Western blots: FIG. 4D). Most of these newly regenerated neuronal structures were localized in the muscular layer, especially in circular muscle and the space between the longitudinal and circular muscular layers (FIGS. 3B-3H and FIGS. 4A-4C; red). Compared with normal control rats (sham controls, no BAC treatment), regenerated PGP9.5-positive neuronal structures in the muscular layer are less ordered (FIG. 4D). The regenerated neurons exhibited various morphological features (shapes and sizes) (FIGS. 12A-12E). BMM-labeled blue fluorescence could not be detected in these regenerated neuron-like structures (FIGS. 3B-3H and FIGS. 4A-4C; red and blue), indicating that these structures had not originated from the grafted BMSC. This result was further confirmed by the observation from the transplantation of GFP-BMSC. The newborn PGP9.5-positive neurons did not co-localize with grafted GFP-BMSC (FIGS. 5A-5D).

2(f) BMSC Transplantation Induced a Dramatic Increase in the Expression of Multiple Neuronal Markers.

Figure 4E:
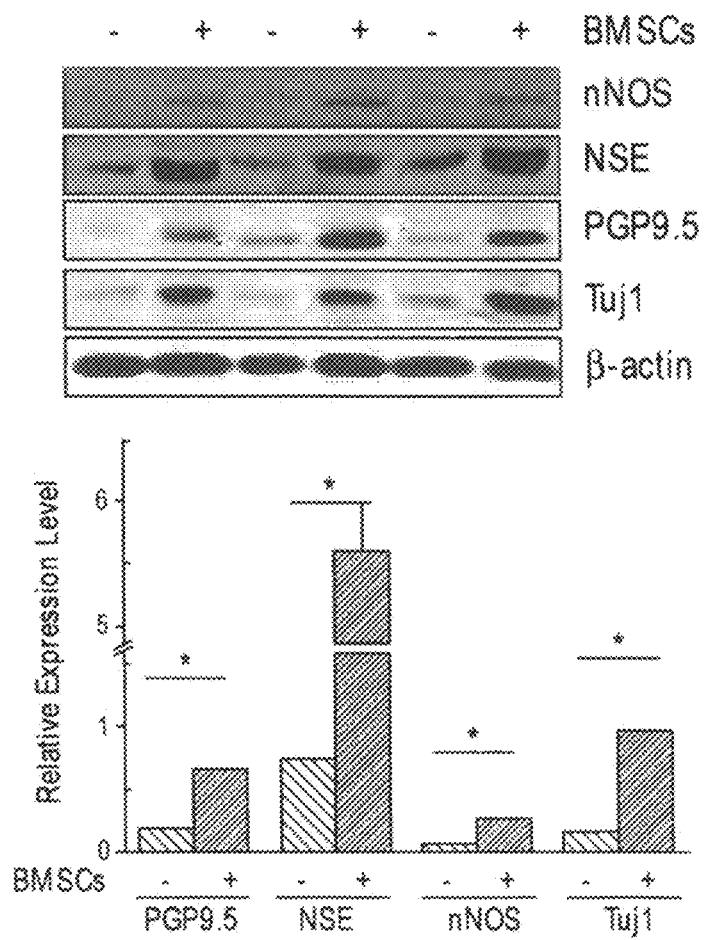
Figure 13A:
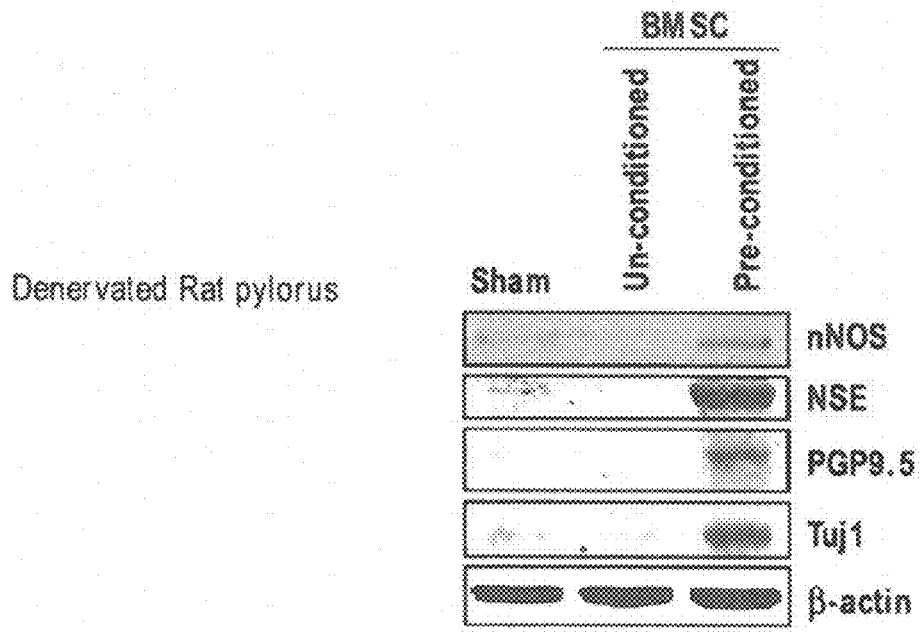
FIGS. 13A-13B. Only preconditioned BMSCs, but not unconditioned BMSCs, promote the expression of neuronal markers. The expression of neuronal markers PGP9.5, NSE, Tuj1 and nNOS, as demonstrated by SDS-PAGE and Western blotting, was increased dramatically in pyloric wall of BAC-treated myenteric nervous ablated rat with pre-conditioned BMSC, but not unconditioned BMSC FIG. 13A. Relative expression level was normalized with β-actin FIG. 13B. Data shown are representative of at least 3 independent experiments, using one-tailed Student's t-test. Error bars denote SEM. *P<0.01.
Figure 13B:
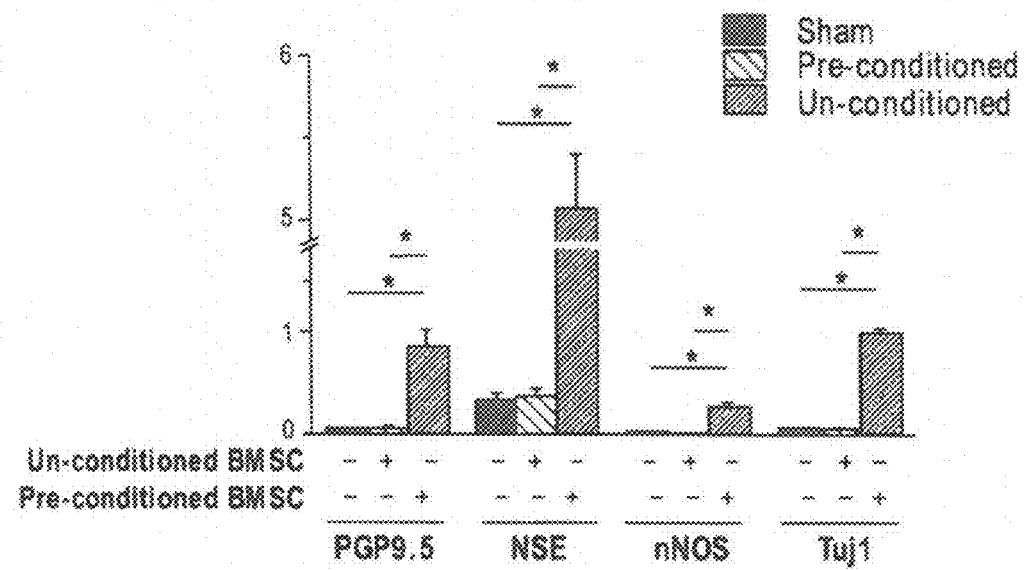

Consistent with immunohistology (FIGS. 3A-3H and 4A-4D, Western blot analyses (FIG. 4E) showed a marked increase in the expression of three neuronal markers (PGP9.5, NSE, Tuj1) and nNOS in the pylorus of denervated rats 28 days after transplantation of in vitro preconditioned BMSC, when compared to those in BAC-treated sham controls. Statistical analysis demonstrated at least a 3-fold increase in the expression of PGP9.5, NSE, Tuj1 and nNOS (FIG. 4E, lower panel). Also consistent with the immunohistological data, the transplantation with unconditioned BMSC led to little change in the expression of these neuronal proteins compared to that with preconditioned BMSC (FIGS. 13A-13B).

2(g) BMSC Transplantation Markedly Restores the EFS-induced Relaxation in Denervated Pylorus.

Figure 6A:
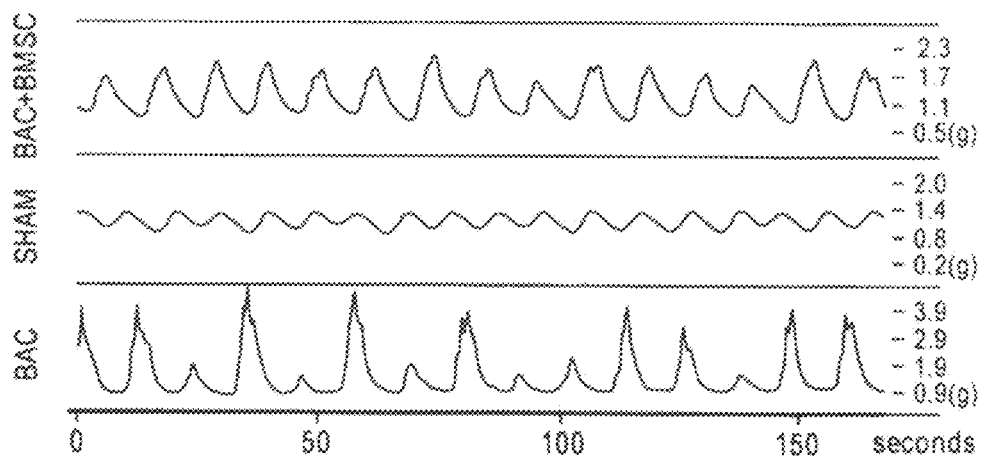
FIGS. 6A-6E. Both basal tension and EFS-induced relaxation of circular denervated muscle strips were significantly improved by BMSC transplantation.
Figure 6B:
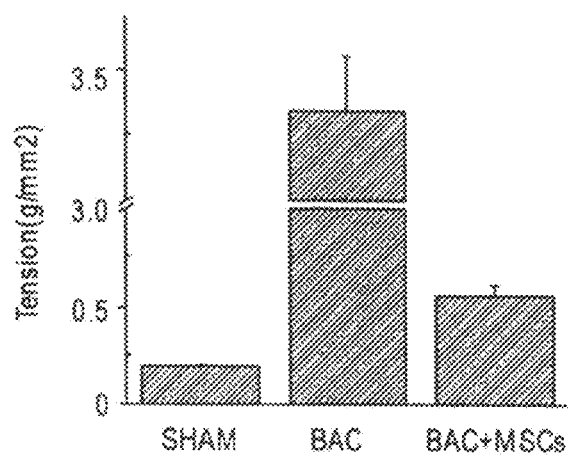
Figure 6C:
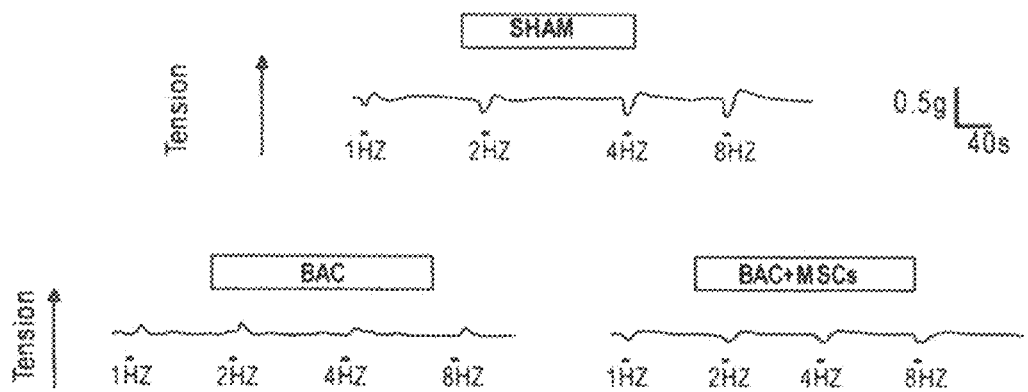
Figure 6D:
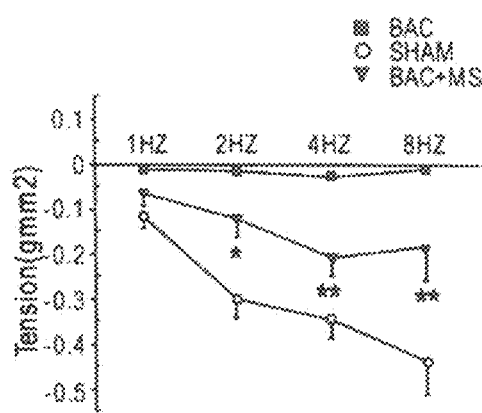
Figure 6E:
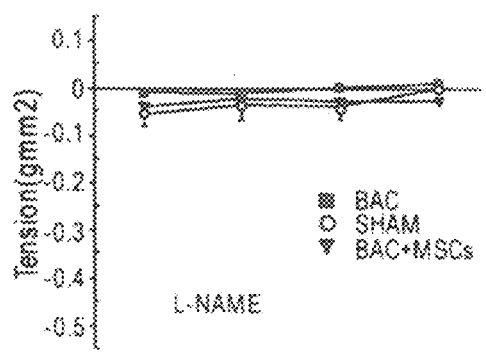

Muscle strips from BAC-ablated rats exhibited increased tension and irregular peaks, when compared to those from control (sham) animals. BMSC transplantation significantly corrected these abnormalities, including both tracing pattern (FIG. 6A,B) and contraction tension (FIG. 6C,D: sham operation vs. BAC-denervated rats with vehicle alone vs. denervated rats with BMSC-transplantation=0.19±0.01 g vs. 3.35±0.21 g vs. 0.55±0.04 g, p<0.01). Specifically, as shown in the representative tracing in responses to increasing frequencies of stimulation (1-8 Hz) (FIG. 6C), EFS-induced frequency-dependent relaxation of the circular pyloric muscle strips isolated from sham group was abolished after BAC treatment. However, in BAC-denervated rats transplanted with preconditioned BMSC, the EFS-induced relaxation was markedly improved (increased), when compared to that from sham BAC-denervated rats (FIG. 6C,D, p<0.01) (or group receiving unconditioned BMSC, data not shown). The NOS inhibitor L-NAME completely blocked this restoration (FIG. 6E).

2(h) "GDNF Positive Feedback" Phenomenon was Observed Both In Vitro and In Vivo.

Figures 7A, 7B:
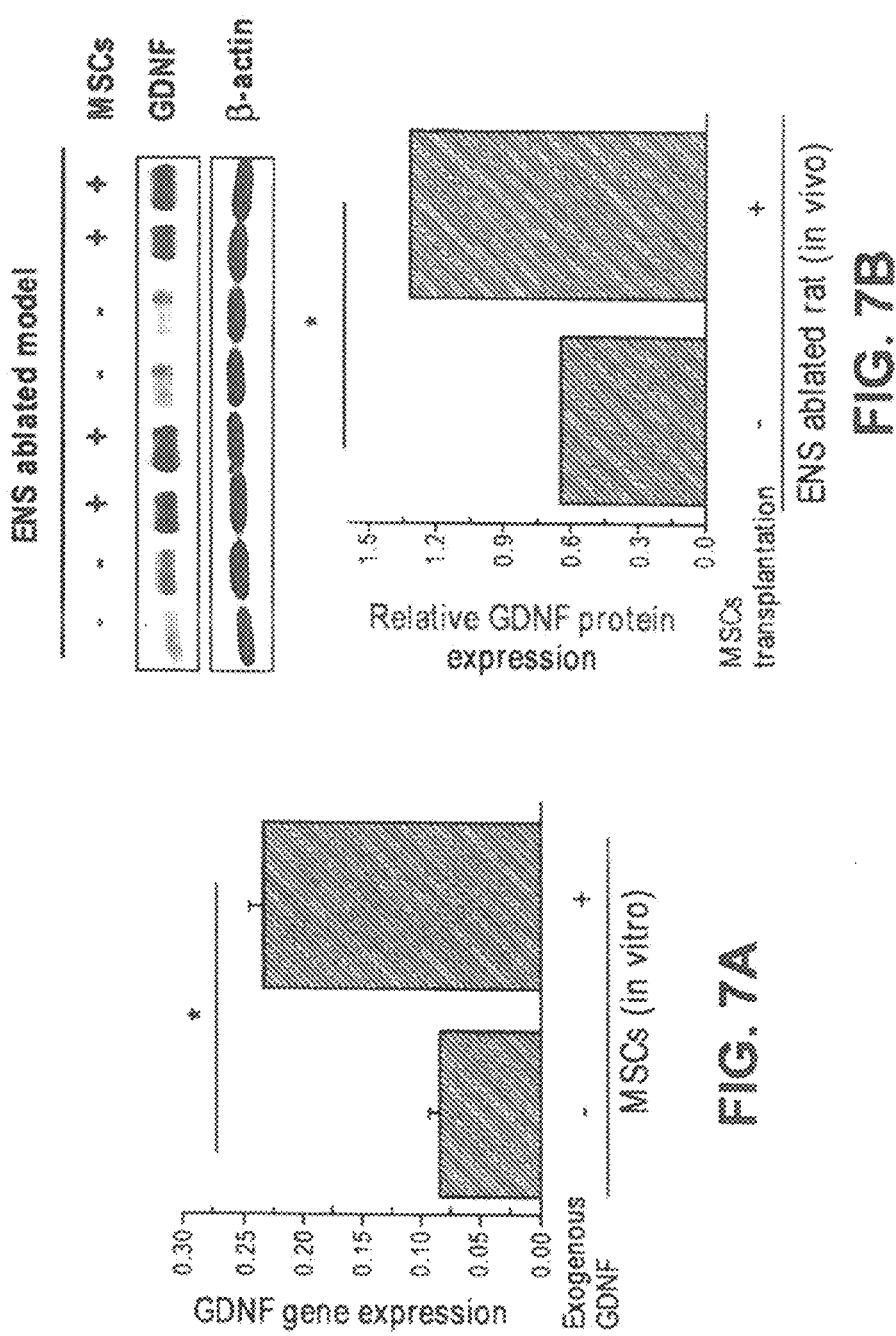
FIGS. 7A-7B. GDNF positive feedback of BMSC maintains a high concentration of GDNF in BAC-treated pylorus.
Figure 14:
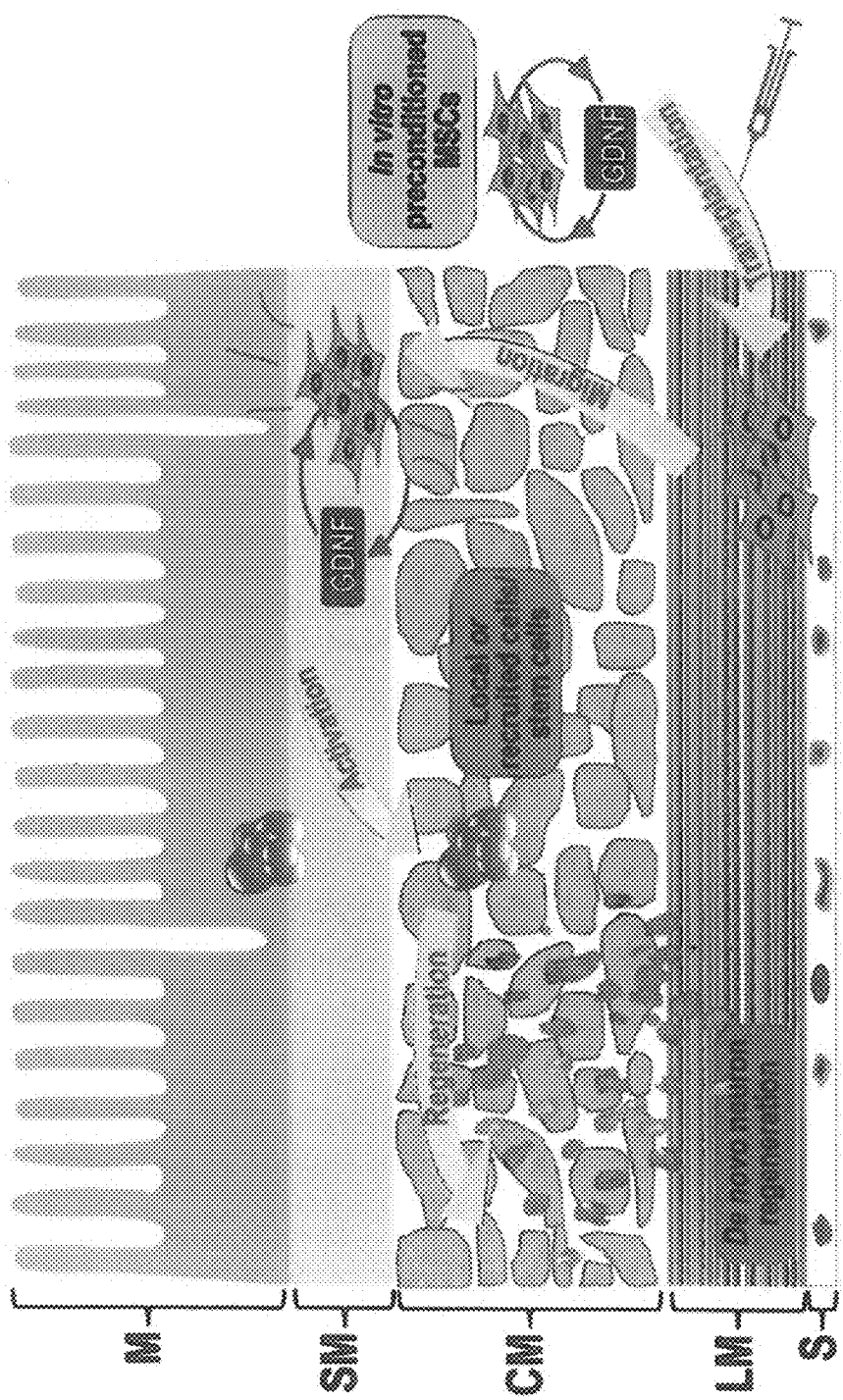
FIG. 14. A schematic illustration of a "GDNF positive feedback mechanism" as a working model in the BMSC-mediated regeneration of enteric neurons.

As a neurotrophic growth factor, GDNF plays a role in the development of the ENS. In rats grafted with in vitro pre-conditioned BMSC, we observed a potential positive-feedback mechanism of endogenous GDNF expression. BMSC endogenously expressed GDNF protein at very low level; however a significantly increased level of endogenous GDNF expression in BMSC was detected after in vitro pre-condition by exogenous GDNF [0.23±0.01 vs. 0.09±0.01 (mean±SEM), FIG. 7A). Furthermore, in vitro pre-conditioned BMSCs induced a sustained and stably high level of in vivo GDNF expression in transplanted rats for 28 days, compared to sham controls (FIG. 7B). This "GDNF positive feedback" model is illustrated in FIG. 14 (see details in Discussion, below).

Example 3: Discussion

The results above demonstrate that allogeneic in vitro pre-conditioned BMSCs are capable of effectively inducing regeneration of enteric neurons and restoring BAC-induced defective gastric contractility. The allogeneic pre-conditioned BMSCs survived and maintained a neuronal phenotype (strongly positive in neuronal markers) in ablated pylorus for at least 28 days in the absence of an immunosuppressive agent or caspase inhibitors. The regenerated neurons did not originate from the transplanted BMSC.

Applying BAC to the serosal surface of the gut is a common method to chemically generate an experimental model of ENS denervation [41,42,48, which are herein incorporated by reference in their entireties]. In 2003, Hanani et al. described the regeneration of nerve fibers and neurons in the BAC-treated area which were thought to have originated from myenteric neurons adjacent to the denervated region [49, which is herein incorporated by reference in its entirety]. However, it was recently reported by Joseph et al., using BrdU incorporation, that no neuron regeneration occurred in the ablated region even months after BAC treatment [50]. To eliminate the possibility raised by Hanani, we extended the length of denervation segment around the ROI (FIG. 2A). It was found that serosal application of 0.5% BAC for 20 minutes to a 3-cm segment led to sufficient and highly reproducible pyloric denervation in the ROI for at least 28 days (FIGS. 2A-2C).

The current knowledge regarding the function of BMSCs in ENS neurogenesis is described in 35,36,51,52, which are herein incorporated by reference in their entireties. While BMSCs have long been considered as a uniquely promising tool for allogenic cell therapy based on their easy accessibility, active cell expansion capacity, high plasticity, and especially their immune privilege during the allogeneic transplantation, post-transplantation survival appears to be a limiting factor for successful anatomical and functional repopulation in the host tissue [7,8,18,53, which are herein incorporated by reference in their entireties]. Surprisingly, however, the present methods resulted in allogeneic BMSC, which survived in a niche for at least 28 days in the absence of immunosuppressive agents or caspase inhibitors. The present disclosure, accordingly, demonstrates a significant practical benefit toward BMSC-based therapy on ENS disorders.

Compared to a previous report [54, which is herein incorporated by reference in its entirety], we achieved a higher efficiency of BMSC transition into a "neuron-like state" as a result of our modified in vitro pre-conditioning protocol (FIGS. 1A-1I,3A-3H & 4A-4E). Phenotype maintenance of in vitro preconditioned BMSC has been considered difficult, most likely due to transdifferentiation [18,19, 22,54, which are herein incorporated by reference in their entireties]. The transdifferentiation ability of BMSCs presents a significant challenge to the development of BMSC-based therapy as it may occur as a consequence of a stress response. The above data show that the in vitro pre-conditioned BMSCs maintained a PGP9.5/Tuj1/HuC/D/nNOS-positive phenotype in the submucosa (predominantly) and muscular layer for at least 28 days. Both BMSC migratory behavior and phenotype indicated that the submucosal layer is a suitable niche for grafted BMSCs.

The present data demonstrated a highly effective regeneration of neurons or neuronal structures in submucosa and particularly the muscle layer by grafted preconditioned BMSC, but not unconditioned BMSC. This result provides strong evidence that preconditioned BMSC initiated the neurogenesis. These data support that efficient pre-differentiation of BMSCs by GDNF/FGCM in vitro before transplantation may be used as an early "priming" or "pre-conditioning" step for neuron regeneration in the denervation model. However, these regenerated neuron-like cells/structures did not originate from grafted BMSC, since they were negative in both fluorescence BBM and GFP (FIGS. 3A-3H, 4A-4E, and 5A-5D).

It is hypothesized that the regenerated neuron-like cells/structures are induced by the in vitro pre-conditioned BMSCs. Without being limited by theory, one possibility is that the grafted BMSC initiated de novo regeneration of new neurons by perhaps attracting local or distant migrating stem cells to the muscle layer. It is further hypothesized that in vitro preconditioned to PGP9.5-positive grafted BMSC may create a "transient niche" at the denervated site by secreting specific signaling molecules or factors. This specific niche "attracts" and then activates the proliferation and differentiation of indwelling or migrating stem cells, leading to de novo neuron regeneration. Recently, Mathur et al has reported that adult midgut progenitors could generate transient niches that determined the intestinal stem cell fate [55]. It is accordingly possible that a "transient niche" created by preconditioned BMSC encouraged growth of neighboring neuron axons into the denervated region through the expression of GDNF or other neuronal factors, and the unconditioned BMSC could not.

To further explore the mechanisms, we analyzed multiple neurotropic factors secreted by grafted BMSC. These could potentially be the BMSC-derived specific factors that contribute to the unique niches and initiate ENS regeneration. GDNF not only functions as a neuron protective factor, but as a factor for the development of the ENS [2,56, which are herein incorporated by reference in their entireties]. Based on our data, we propose a "BMSC-initiated GDNF positive-feedback" mechanism, as illustrated in FIG. 14 that at least partially mediates the initiation and expansion of new neurons. A similar phenomenon was reported in kidney-derived MSC [57, which is herein incorporated by reference in its entirety]. Transient increase of GDNF expression in acute injury was previously reported [58,59, which are herein incorporated by reference in their entireties], started within 30 min after injury, peaked within 3 h, and then decreased rapidly after 24 h. The above-described data demonstrated that a high level of GDNF was expressed in vivo 28 days post-transplantation in the denervated region of rats transplanted with preconditioned BMSC, but not in the sham control groups. This would suggest that the increase of GDNF as described herein was not due to the potential injury-induced elevation of GDNF. Therefore, it is hypothesized that GDNF produced by grafted BMSC that were pre-conditioned in vitro prior to transplantation might provide a feedback mechanism after transplantation to maintain a high level of local GDNF, which creates niches that favors or facilitates the differentiation of new neuron or neuron-like cells from an undefined cell source (FIG. 14). In addition, our observation that grafted BMSC stably maintained a neuronal phenotype for at least 28 days post-transplantation would suggest that BMSC have long-lasting effects on promoting neuron regeneration.

The contractility/tension of pyloric muscle was markedly improved 28 days post BAC-induced pylorus denervation. This functional restoration of muscular contractility strongly demonstrates the therapeutic potential of BMSC.

In summary, it has been demonstrated that in vitro-preconditioned BMSCs promote de novo nerve regeneration and restore muscle contractility in pylorus-denervated rats through a GDNF positive feedback mechanism. These data provide a novel concept for the mechanism responsible for BMSC-induced neuron regeneration and also a strong proof-of-principle for clinical application of BMSC-based therapy in ENS-related disorders.

REFERENCES

1. Laranjeira C, Pachnis V (2009) Enteric nervous system development: Recent progress and future challenges. Auton Neurosci 151: 61-69.
2. Heanue T A, Pachnis V (2007) Enteric nervous system development and Hirschsprung's disease: advances in genetic and stem cell studies. Nat Rev Neurosci 8: 466-479.
3. Camilleri M, Cowen T, Koch T R (2008) Enteric neurodegeneration in ageing. Neurogastroenterol Motil 20: 185-196.
4. Lebouvier T, Chaumette T, Paillusson S, Duyckaerts C, Bruley des Varannes S, et al. (2009) The second brain and Parkinson's disease. Eur J Neurosci 30: 735-741.
5. Pasricha P J (2007) Desperately seeking serotonin . . . . A commentary on the withdrawal of tegaserod and the state of drug development for functional and motility disorders. Gastroenterology 132: 2287-2290.
6. Becker L, Mashimo H (2009) Further promise of stem cells therapies in the enteric nervous system. Gastroenterology 136: 2055-2058.
7. Kulkarni S, Becker L, Pasricha P J (2012) Stem cell transplantation in neurodegenerative disorders of the gastrointestinal tract: future or fiction? Gut 61:613-621.
8. Garbossa D, Boido M, Fontanella M, Fronda C, Ducati A, et al. (2012) Recent therapeutic strategies for spinal cord injury treatment: possible role of stem cells. Neurosurg Rev 35: 293-311; discussion 311.
9. Koch P, Opitz T, Steinbeck J A, Ladewig J, Brustle O (2009) A rosette-type, self-renewing human ES cell-derived neural stem cell with potential for in vitro instruction and synaptic integration. Proc Natl Acad Sci USA 106: 3225-3230.
10. Kawaguchi J, Nichols J, Gierl M S, Faial T, Smith A (2010) Isolation and propagation of enteric neural crest progenitor cells from mouse embryonic stem cells and embryos. Development 137: 693-704.
11. Hu B Y, Weick J P, Yu J, Ma L X, Zhang X Q, et al. (2010) Neural differentiation of human induced pluripotent stem cells follows developmental principles but with variable potency. Proc Natl Acad Sci USA 107: 4335-4340.
12. Micci M A, Kahrig K M, Simmons R S, Sarna S K, Espejo-Navarro M R, et al. (2005) Neural stem cell transplantation in the stomach rescues gastric function in neuronal nitric oxide synthase-deficient mice. Gastroenterology 129: 1817-1824.
13. Dupin E, Sommer L (2012) Neural crest progenitors and stem cells: from early development to adulthood. Dev Biol 366: 83-95.
14. Metzger M, Caldwell C, Barlow A J, Burns A J, Thapar N (2009) Enteric nervous system stem cells derived from human gut mucosa for the treatment of aganglionic gut disorders. Gastroenterology 136: 2214-2225 e2211-2213.
15. Lindley R M, Hawcutt D B, Connell M G, Almond S L, Vannucchi M G, et al. (2008) Human and mouse enteric nervous system neurosphere transplants regulate the function of aganglionic embryonic distal colon. Gastroenterology 135: 205-216 e206.
16. Ben-David U, Benvenisty N (2011) The tumorigenicity of human embryonic and induced pluripotent stem cells. Nat Rev Cancer 11: 268-277.
17. Micci M A, Pasricha P J (2007) Neural stem cells for the treatment of disorders of the enteric nervous system: strategies and challenges. Dev Dyn 236: 33-43.
18. Lindvall O, Kokaia Z (2010) Stem cells in human neurodegenerative disorders—time for clinical translation? J Clin Invest 120: 29-40.
19. Scuteri A, Miloso M, Foudah D, Orciani M, Cavaletti G, et al. (2011) Mesenchymal stem cells neuronal differentiation ability: a real perspective for nervous system repair? Curr Stem Cell Res Ther 6: 82-92.
20. Trzaska K A, King C C, Li K Y, Kuzhikandathil E V, Nowycky M C, et al. (2009) Brain-derived neurotrophic factor facilitates maturation of mesenchymal stem cell-derived dopamine progenitors to functional neurons. J Neurochem 110: 1058-1069.
21. Greco S J, Zhou C, Ye J H, Rameshwar P (2007) An interdisciplinary approach and characterization of neuronal cells transdifferentiated from human mesenchymal stem cells. Stem Cells Dev 16: 811-826.
22. Lu P, Blesch A, Tuszynski M H (2004) Induction of bone marrow stromal cells to neurons: differentiation, transdifferentiation, or artifact? J Neurosci Res 77: 174-191.
23. Singer N G, Caplan A I (2011) Mesenchymal stem cells: mechanisms of inflammation. Annu Rev Pathol 6: 457-478.
24A. Jun Zhang, Xiaowen Huang, Haijun Wang, Xiaoyan Liu, Tao Zhang, Yunchuan Wang and Dahai Hu (2015) The challenges and promises of allogeneic mesenchymal stem cells for use as a cell-based therapy. Stem Cell Research & Therapy 6:234, pages 1-7.
24B. Ankrum J A, Ong J F, Karp J M (2014) Mesenchymal stem cells: immune evasive, not immune privileged. Nat. Biotechnol. 32:252-60. doi: 10.1038/nbt.2816.
25. Vercelli A, Mereuta O M, Garbossa D, Muraca G, Mareschi K, et al. (2008) Human mesenchymal stem cell transplantation extends survival, improves motor performance and decreases neuroinflammation in mouse model of amyotrophic lateral sclerosis. Neurobiol Dis 31: 395-405.
26. Ninomiya K, Iwatsuki K, Ohnishi Y, Ohkawa T, Yoshimine T. (2015) Intranasal delivery of bone marrow stromal cells to spinal cord lesions. J Neurosurg Spine. 1:111-9.
27. Shichinohe H, Ishihara T, Takahashi K, Tanaka Y, Miyamoto M, et al. (2015) Bone marrow stromal cells 27. rescue ischemic brain by trophic effects and phenotypic change toward neural cells. Neurorehabil Neural Repair 29: 80-89.
28. Tanna T, Sachan V (2014) Mesenchymal stem cells: potential in treatment of neurodegenerative diseases. Curr Stem Cell Res Ther 9: 513-521.
29. Dasari V R, Veeravalli K K, Dinh D H (2014) Mesenchymal stem cells in the treatment of spinal cord injuries: A review. World J Stem Cells 6: 120-133.
30. Maltman D J, Hardy S A, Przyborski S A (2011) Role of mesenchymal stem cells in neurogenesis and nervous system repair. Neurochem Int 59: 347-356.
31. Wurmser A E, Gage F H (2002) Stem cells: cell fusion causes confusion. Nature 416: 485-487.
32. Sanges D, Lluis F, Cosma M P (2011) Cell-fusion-mediated reprogramming: pluripotency or transdifferentiation? Implications for regenerative medicine. Adv Exp Med Biol 713: 137-159.
33. Metzger M (2010) Neurogenesis in the enteric nervous system. Arch Ital Biol 148: 73-83.
34. Houghton J, Stoicov C, Nomura S, Rogers A B, Carlson J, et al. (2004) Gastric cancer originating from bone marrow-derived cells. Science 306: 1568-1571.
35. Kawahara I, Kuniyasu H, Matsuyoshi H, Goto K, Obata K, et al. (2012) Comparison of effects of a selective 5-HT reuptake inhibitor versus a 5-HT4 receptor agonist on in vivo neurogenesis at the rectal anastomosis in rats. Am J Physiol Gastrointest Liver Physiol 302: G588-597.
36. Wood J D (2011) Enteric nervous system neuropathy: repair and restoration. Curr Opin Gastroenterol 27: 106-111.
37. Herrmann J L, Wang Y, Abarbanell A M, Weil B R, Tan J, et al. (2010) Preconditioning mesenchymal stem cells with transforming growth factor-alpha improves mesenchymal stem cell-mediated cardioprotection. Shock 33: 24-30.
38. Liu Y, Jiang X, Zhang X, Chen R, Sun T, et al. (2011) Dedifferentiation-reprogrammed mesenchymal stem cells with improved therapeutic potential. Stem Cells 29: 2077-2089.
39. Boopathy A V, Pendergrass K D, Che P L, Yoon Y S, Davis M E (2013) Oxidative stress-induced Notch1 signaling promotes cardiogenic gene expression in mesenchymal stem cells. Stem Cell Res Ther 4: 43.
40. Bondurand N, Natarajan D, Thapar N, Atkins C, Pachnis V (2003) Neuron and glia generating progenitors of the mammalian enteric nervous system isolated from foetal and postnatal gut cultures. Development 130: 6387-6400.
41. Liu W, Wu R D, Dong Y L, Gao Y M (2007) Neuroepithelial stem cells differentiate into neuronal phenotypes and improve intestinal motility recovery after transplantation in the aganglionic colon of the rat. Neurogastroenterol Motil 19: 1001-1009.
42. Higham A, Vaillant C, Yegen B, Thompson D G, Dockray G J (1997) Relation between cholecystokinin and antral innervation in the control of gastric emptying in the rat. Gut 41: 24-32.
43. Long Y, Liu Y, Tong J, Qian W, Hou X (2010) Effectiveness of trimebutine maleate on modulating intestinal hypercontractility in a mouse model of postinfectious irritable bowel syndrome. Eur J Pharmacol 636: 159-165.
44. Depoortere I, De Winter B, Thijs T, De Man J, Pelckmans P, et al. (2005) Comparison of the gastroprokinetic effects of ghrelin, GHRP-6 and motilin in rats in vivo and in vitro. Eur J Pharmacol 515: 160-168.
45. Lin R, Murtazina R, Cha B, Chakraborty M, Sarker R, et al. (2011) D-glucose acts via sodium/glucose cotransporter 1 to increase NHE3 in mouse jejunal brush border by a Na+/H+ exchange regulatory factor 2-dependent process. Gastroenterology 140: 560-571.
46. Alex P, Ye M, Zachos N C, Sipes J, Nguyen T, et al. (2010) Clcn5 knockout mice exhibit novel immunomodulatory effects and are more susceptible to dextran sulfate sodium-induced colitis. J Immunol 184: 3988-3996.
47. Lin R, Ma H, Ding Z, Shi W, Qian W, et al. (2013) Bone marrow-derived mesenchymal stem cells favor the immunosuppressive T cells skewing in a Helicobacter pylori model of gastric cancer. Stem Cells Dev 22: 2836-2848.
48. Gaumnitz E A, Bass P, Osinski M A, Sweet M A, Singaram C (1995) Electrophysiological and pharmacological responses of chronically denervated lower esophageal sphincter of the opossum. Gastroenterology 109: 789-799.
49. Hanani M, Ledder O, Yutkin V, Abu-Dalu R, Huang T Y, et al. (2003) Regeneration of myenteric plexus in the mouse colon after experimental denervation with benzalkonium chloride. J Comp Neurol 462: 315-327.
50. Joseph N M, He S, Quintana E, Kim Y G, Nunez G, et al. (2011) Enteric glia are multipotent in culture but primarily form glia in the adult rodent gut. J Clin Invest 121: 3398-3411.
51. Matsuyoshi H, Kuniyasu H, Okumura M, Misawa H, Katsui R, et al. (2010) A 5-HT(4)-receptor activation-induced neural plasticity enhances in vivo reconstructs of enteric nerve circuit insult. Neurogastroenterol Motil 22: 806-813, e226.
52. Liu M T, Kuan Y H, Wang J, Hen R, Gershon M D (2009) 5-HT4 receptor-mediated neuroprotection and neurogenesis in the enteric nervous system of adult mice. J Neurosci 29: 9683-9699.
53. Micci M A, Pattillo M T, Kahrig K M, Pasricha P J (2005) Caspase inhibition increases survival of neural stem cells in the gastrointestinal tract. Neurogastroenterol Motil 17: 557-564.
54. Rismanchi N, Floyd C L, Berman R F, Lyeth B G (2003) Cell death and long-term maintenance of neuron-like state after differentiation of rat bone marrow stromal cells: a comparison of protocols. Brain Res 991: 46-55.
55. Mathur D, Bost A, Driver I, Ohlstein B (2010) A transient niche regulates the specification of Drosophila intestinal stem cells. Science 327: 210-213.
56. Shepherd I T, Pietsch J, Elworthy S, Kelsh R N, Raible D W (2004) Roles for GFRalpha1 receptors in zebrafish enteric nervous system development. Development 131: 241-249.
57. Shi H, Patschan D, Dietz G P, Bahr M, Plotkin M, et al. (2008) Glial cell line-derived neurotrophic growth factor increases motility and survival of cultured mesenchymal stem cells and ameliorates acute kidney injury. Am J Physiol Renal Physiol 294: F229-235.
58. Satake K, Matsuyama Y, Kamiya M, Kawakami H, Iwata H, et al. (2000) Up-regulation of glial cell line-derived neurotrophic factor (GDNF) following traumatic spinal cord injury. Neuroreport 11: 3877-3881.
59. Kao C H, Chen S H, Chio C C, Chang C K, Lin M T (2008) Exogenous administration of glial cell line-derived neurotrophic factor improves recovery after spinal cord injury. Resuscitation 77: 395-400.

What is claimed is:

1. A composition comprising:
    an isolated in vitro pre-conditioned population of adult bone marrow derived mesenchymal stem cells (BMSCs),
        wherein at least 80% of the in vitro pre-conditioned BMSC population express PGP9.5 and NSE,
        wherein at least 70% of the in vitro pre-conditioned BMSC population express Tuj1 and HuC/D,
        wherein at least 75% of the in vitro pre-conditioned BMSC population express neuronal nitric oxide synthase (nNOS), and
        wherein the BMSCs promote de novo regeneration of neurons not originated from the BMSCs when the BMSCs are administered to a subject.

2. The composition of claim 1, wherein the in vitro pre-conditioning comprises:
    providing a population of mesenchymal stem cells from a bone marrow;
    culturing the population of mesenchymal stem cells in a medium comprising a glial cell derived neurotrophic factor and a fetal gut culture medium.

3. The composition of claim 1, wherein about 80% of the cells in the in vitro pre-conditioned BMSC population express PGP9.5, about 80% of the cells in the in vitro pre-conditioned BMSC population express NSE, about 75% of the cells in the in vitro pre-conditioned BMSC population express Tuj1, about 73% of the cells in the in vitro pre-conditioned BMSC population express HuC/D and about 75% of the in vitro pre-conditioned BMSC population express nNOS.

4. The composition of claim 1, wherein the in vitro pre-conditioned BMSCs are capable of maintaining a neuronal-like phenotype in vivo for at least 28 days.

5. The composition of claim 1, wherein the in vitro pre-conditioned BMSCs are human cells.

6. The composition of claim 1, further comprising a pharmaceutically acceptable carrier.

7. The composition of claim 1, wherein the in vitro pre-conditioned BMSC population are labeled with a bio-imaging agent.

8. A method of treating an enteric nervous system disorder comprising:
    administering to a subject in need thereof a pharmaceutical composition comprising an isolated in vitro preconditioned population of adult bone marrow derived mesenchymal stem cells (BMSCs), wherein at least 80% of the in vitro pre-conditioned BMSC population express PGP9.5 and NSE, wherein at least 70% of the in vitro pre-conditioned BMSC population express Tuj1 and HuC/D, wherein at least 75% of the in vitro pre-conditioned BMSC population express neuronal nitric oxide synthase (nNOS), and wherein the BMSCs promote de novo regeneration of neurons not originated from the BMSCs when the BMSCs are administered to a subject and a pharmaceutically acceptable carrier.

9. The method of claim 8, wherein the enteric nervous system disorder is selected from the group consisting of a dysmotility syndrome, a diabetic gastroparesis, an intestinal pseudo-obstruction of motility, and neuronal loss in an enteric nervous system.

10. The method of claim 8, wherein the dysmotility syndrome is selected from the group consisting of achalasia, gastro-esophageal reflux disease, delayed emptying of the stomach, abdominal pain, bloating, diarrhea and constipation.

11. The method of claim 10, wherein the dysmotility syndrome is a congenital dysmotility syndrome.

12. The method of claim 11, wherein the congenital dysmotility syndrome is Hirschsprung disease.

13. The method of claim 8, wherein the pharmaceutical composition is administered into a gastrointenstinal tract of the subject.

14. The method of claim 8, wherein the pharmaceutical composition is administered endoscopically to the subject.

15. The method of claim 8, where the pharmaceutical composition is administered into a pylorus of the subject.

16. The method of claim 15, wherein the pharmaceutical composition is administered into a submucosal layer of the pylorus.

17. A method of preparing mesenchymal stem cells exhibiting a neuronal phenotype which method comprises:
isolating mesenchymal stem cells from an adult bone marrow;
culturing the mesenchymal stem cells in a medium comprising glial cell derived neurotrophic factor and a fetal gut culture medium to thereby obtain an isolated in vitro pre-conditioned population of adult bone marrow derived mesenchymal stem cells (BMSCs),
wherein at least 80% of the in vitro pre-conditioned BMSC population express PGP9.5 and NSE,
wherein at least 70% of the in vitro pre-conditioned BMSC population express Tuj1 and HuC/D,
wherein at least 75% of the in vitro pre-conditioned BMSC population express neuronal nitric oxide synthase (nNOS), and
wherein the BMSCs promote de novo regeneration of neurons not originated from the BMSCs when the BMSCs are administered to a subject.

18. The method of claim 17, wherein the mesenchymal stem cells maintain the neuronal phenotype for at least 28 days in vivo.

19. The method of claim 17, wherein about 80% of the cells in the in vitro pre-conditioned BMSC population express PGP9.5, about 80% of the cells in the in vitro pre-conditioned BMSC population express NSE, about 75% of the cells in the in vitro pre-conditioned BMSC population express Tuj1, about 73% of the cells in the in vitro pre-conditioned BMSC population express HuC/D and about 75% of the in vitro pre-conditioned BMSC population express nNOS.

20. The method of claim 17, wherein the mesenchymal stem cells are human cells.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: GDNF Primer

<400> SEQUENCE: 1
tgaagttatg ggatgtcgtg g                                        21

<210> SEQ ID NO 2
<211> LENGTH: 20
<212> TYPE: DNA
<213> ORGANISM: Artificial Sequence
<220> FEATURE:
<223> OTHER INFORMATION: GDNF Primer

<400> SEQUENCE: 2
gccgcttgtt tatctggtga                                          20

<210> SEQ ID NO 3
<211> LENGTH: 18
<212> TYPE: DNA
<213> ORGANISM: Artificial Sequence
<220> FEATURE:
<223> OTHER INFORMATION: Beta-actin (control)

<400> SEQUENCE: 3
agggaaatcg tgcgtgac                                            18

<210> SEQ ID NO 4
<211> LENGTH: 18
<212> TYPE: DNA
<213> ORGANISM: Artificial Sequence
<220> FEATURE:
<223> OTHER INFORMATION: beta-actin (control)

<400> SEQUENCE: 4
acccacggaa ggaaggct                                            18
```